(12) United States Patent
Ganz et al.

(10) Patent No.: US 8,435,941 B2
(45) Date of Patent: May 7, 2013

(54) MINI-HEPCIDIN PEPTIDES AND METHODS OF USING THEREOF

(75) Inventors: Tomas Ganz, Los Angeles, CA (US); Elizabeta Nemeth, Los Angeles, CA (US); Gloria Preza, Los Angeles, CA (US); Piotr Pawel Ruchala, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/131,792

(22) PCT Filed: Dec. 4, 2009

(86) PCT No.: PCT/US2009/066711
§ 371 (c)(1),
(2), (4) Date: May 31, 2011

(87) PCT Pub. No.: WO2010/065815
PCT Pub. Date: Jun. 10, 2010

(65) Prior Publication Data
US 2012/0040894 A1     Feb. 16, 2012

Related U.S. Application Data

(60) Provisional application No. 61/120,277, filed on Dec. 5, 2008.

(51) Int. Cl.
*A61K 38/04*  (2006.01)
(52) U.S. Cl.
USPC ......... 514/5.4; 514/13.5; 514/21.8; 514/21.7; 514/21.6
(58) Field of Classification Search .................. None
See application file for complete search history.

(56) References Cited

U.S. PATENT DOCUMENTS

| | | | |
|---|---|---|---|
| 5,739,274 A * | 4/1998 | Pang et al. | 530/324 |
| 2007/0134746 A1 | 6/2007 | Kulaksiz | |
| 2008/0213277 A1 | 9/2008 | Sasu et al. | |
| 2010/0330595 A1 | 12/2010 | Kulaksiz | |
| 2011/0287448 A1 | 11/2011 | Kulaksiz | |

FOREIGN PATENT DOCUMENTS

WO     2004/058044 A2     7/2004

OTHER PUBLICATIONS

PDB file of protein 2A9H_E, Charybdotoxin.*
Naini A. A. et al; "Interaction of Ca2+-activated K+ channels with refolded charybdotoxins mutated at a central interaction residue." Neuropharmacology (1996) 35 (7) p. 915-921.*
Supplementary European Search Report received in EP09831165.7, mailed Apr. 5, 2012.
Preza, G. et al. (2011) "Minihepcidins are Rationally Designed Small Peptides that Mimic Hepcidin Activity in Mince and May be Useful for the Treatment of Iron Overload" Journal of Clinical Investigation, 121(12): 4880-4888.
Nemeth, E. et al. (2006) "The N-terminus of Hepcidin is Essential for its Interaction with Ferroportin: Structure-Function Study" Blood, 107(1): 328-333.
Hunter, H. et al. (2002) "The Solution Structure of Human Hepcidin, a Peptide Hormone with Antimicrobial Activity that is Involved in Iron Uptake and Hereditary Hemochromatosis" The Journal of Biological Chemistry, 227(4):37597-37603.
Carstens, B.B. (2009) "The Analysis of the Interaction between Hepcidin and Ferroportin" University of Tromsø, http://www.ub.uit.no/munin/bitstream/10037/2178/1/thesis.pdf.
Young, B. et al. (2009) "Hepcidin for Clinicians" Clin J Am Soc Nephrol., 4(8): 1384-1387.
NCBI database HAMP Hepcidin Antimicrobial Peptide [*Homo sapiens*], Gene ID: 57817) Aug. 4, 2010. http://www.ncbi.nlm.nih.gov/sites/entrez?db=gene&cmd=search&term=57817&RID=6PWTUDE011&log$=geneexplicitprot&blast_rank=10.
International Search Report received in PCT/US2009/066711, mailed Aug. 23, 2010.
Written Opinion of the International Searching Authority received in PCT/US2009/066711, mailed Aug. 23, 2010.

\* cited by examiner

*Primary Examiner* — Cecilia J Tsang
*Assistant Examiner* — Fred Reynolds
(74) *Attorney, Agent, or Firm* — Suzannah K. Sundby, Esq.; Smith, Gambrell & Russell, LLP

(57) ABSTRACT

Disclosed herein are peptides which exhibit hepcidin activity and methods of making and using thereof.

18 Claims, 6 Drawing Sheets

SEQUENCE LISTING

<160> NUMBER OF SEQ ID NOS: 15

<210> SEQ ID NO 1
<211> LENGTH: 25
<212> TYPE: PRT
<213> ORGANISM: Homo sapiens

<400> SEQUENCE: 1

Asp Thr His Phe Pro Ile Cys Ile Phe Cys Cys Gly Cys Cys His Arg
1               5                   10                  15

Ser Lys Cys Gly Met Cys Cys Lys Thr
            20                  25

<210> SEQ ID NO 2
<211> LENGTH: 10
<212> TYPE: PRT
<213> ORGANISM: Homo sapiens

<400> SEQUENCE: 2

Asp Thr His Phe Pro Ile Cys Ile Phe Cys
1               5                   10

<210> SEQ ID NO 3
<211> LENGTH: 4
<212> TYPE: PRT
<213> ORGANISM: Homo sapiens

<400> SEQUENCE: 3

Phe Pro Ile Cys
1

<210> SEQ ID NO 4
<211> LENGTH: 5
<212> TYPE: PRT
<213> ORGANISM: Homo sapiens

<400> SEQUENCE: 4

His Phe Pro Ile Cys
1               5

<210> SEQ ID NO 5
<211> LENGTH: 6
<212> TYPE: PRT
<213> ORGANISM: Homo sapiens

<400> SEQUENCE: 5

His Phe Pro Ile Cys Ile
1               5

<210> SEQ ID NO 6
<211> LENGTH: 7
<212> TYPE: PRT
<213> ORGANISM: Homo sapiens

<400> SEQUENCE: 6

His Phe Pro Ile Cys Ile Phe
1               5

<210> SEQ ID NO 7
<211> LENGTH: 7
<212> TYPE: PRT
<213> ORGANISM: Homo sapiens

<400> SEQUENCE: 7

Asp Thr His Phe Pro Ile Cys
1               5

<210> SEQ ID NO 8
<211> LENGTH: 8
<212> TYPE: PRT
<213> ORGANISM: Homo sapiens

<400> SEQUENCE: 8

Asp Thr His Phe Pro Ile Cys Ile
1               5

```
<210> SEQ ID NO 9
<211> LENGTH: 9
<212> TYPE: PRT
<213> ORGANISM: Homo sapiens

<400> SEQUENCE: 9

Asp Thr His Phe Pro Ile Cys Ile Phe
1               5

<210> SEQ ID NO 10
<211> LENGTH: 10
<212> TYPE: PRT
<213> ORGANISM: Homo sapiens

<400> SEQUENCE: 10

Asp Thr His Phe Pro Ile Ala Ile Phe Cys
1               5                   10

<210> SEQ ID NO 11
<211> LENGTH: 9
<212> TYPE: PRT
<213> ORGANISM: Homo sapiens

<400> SEQUENCE: 11

Asp Thr His Ala Pro Ile Cys Ile Phe
1               5

<210> SEQ ID NO 12
<211> LENGTH: 9
<212> TYPE: PRT
<213> ORGANISM: Homo sapiens

<400> SEQUENCE: 12

Asp Thr His Phe Pro Ile Ala Ile Phe
1               5

<210> SEQ ID NO 13
<211> LENGTH: 9
<212> TYPE: PRT
<213> ORGANISM: Homo sapiens

<400> SEQUENCE: 13

Asp Thr His Phe Pro Ile Ser Ile Phe
1               5

<210> SEQ ID NO 14
<211> LENGTH: 10
<212> TYPE: PRT
<213> ORGANISM: Homo sapiens
<220> FEATURE:
<221> NAME/KEY: DISULFID
<222> LOCATION: (1)..(8)

<400> SEQUENCE: 14

Cys Asp Thr His Phe Pro Ile Cys Ile Phe
1               5                   10

<210> SEQ ID NO 15
<211> LENGTH: 8
<212> TYPE: PRT
<213> ORGANISM: Homo sapiens
<220> FEATURE:
<221> NAME/KEY: DISULFID
<222> LOCATION: (1)..(6)
```

```
<400> SEQUENCE: 15

Cys His Phe Pro Ile Cys Ile Phe
1               5
```

MINI-HEPCIDIN PEPTIDES AND METHODS OF USING THEREOF

CROSS-REFERENCE TO RELATED APPLICATIONS

This application claims the benefit of U.S. Provisional Application Ser. No. 61/120,277, filed 5 Dec. 2008, which is herein incorporated by reference in its entirety.

ACKNOWLEDGEMENT OF GOVERNMENT SUPPORT

This invention was made with Government support of Grant Nos. DK 075378 and DK 065029, awarded by the National Institutes of Health. The Government has certain rights in this invention.

BACKGROUND OF THE INVENTION

1. Field of the Invention

The present invention generally relates to peptides which exhibit hepcidin activity.

2. Description of the Related Art

Hepcidin, a peptide hormone produced by the liver, is a regulator of iron homeostasis in humans and other mammals. Hepcidin acts by binding to its receptor, the iron export channel ferroportin, and causing its internalization and degradation. Human hepcidin is a 25-amino acid peptide (Hep25). See Krause et al. (2000) FEBS Lett 480:147-150, and Park et al. (2001) J Biol Chem 276:7806-7810. The structure of the bioactive 25-amino acid form of hepcidin is a simple hairpin with 8 cysteines that form 4 disulfide bonds as described by Jordan et al. (2009) J Biol Chem 284:24155-67. The N terminal region is required for iron-regulatory function, and deletion of 5 N-terminal amino acid residues results in a loss of iron-regulatory function. See Nemeth et al. (2006) Blood 107:328-33.

Abnormal hepcidin activity is associated with iron overload diseases which include hereditary hemochromatosis and iron-loading anemias. Hereditary hemochromatosis (HH) is a genetic iron overload disease that is mainly caused by hepcidin deficiency, or very rarely by hepcidin resistance. This allows excessive absorption of iron from the diet and development of iron overload. Clinical manifestations of HH may include liver disease (hepatic cirrhosis, hepatocellular carcinoma), diabetes, and heart failure. Currently, the only treatment for HH is regular phlebotomy, which is effective but very burdensome for the patients.

Iron-loading anemias are hereditary anemias with ineffective erythropoiesis such as β-thalassemia, which are accompanied by severe iron overload. Complications from iron overload are the main cause of morbidity and mortality for these patients. Hepcidin deficiency is the main cause of iron overload in untransfused patients, and contributes to iron overload in transfused patients. The current treatment for iron overload in these patients is iron chelation which is very burdensome, sometimes ineffective and accompanied by frequent side effects.

SUMMARY OF THE INVENTION

The present invention generally relates to peptides which exhibit hepcidin activity and methods of using thereof.

The present invention provides peptides, which may be isolated and/or purified, comprising, consisting essentially or consisting of the following structural formula

A1-A2-A3-A4-A5-A6-A7-A8-A9-A10 wherein

A1 is Asp, Glu, pyroglutamate, Gln, Asn, or an unnatural amino acid commonly used as a substitute thereof;

A2 is Thr, Ser, Val, Ala or an unnatural amino acid commonly used as a substitute thereof;

A3 is His, Asn, Arg, or an unnatural amino acid commonly used as a substitute thereof;

A4 is Phe, Leu, Ile, Trp, Tyr or an unnatural amino acid commonly used as a substitute thereof which includes cyclohexylalanine;

A5 is Pro, Ser, or an unnatural amino acid commonly used as a substitute thereof;

A6 is Ile, Leu, Val, or an unnatural amino acid commonly used as a substitute thereof;

A7 is Cys, Ser, Ala, or an unnatural amino acid commonly used as a substitute thereof which includes S-tertiary butyl-cysteine;

A8 is Ile, Leu, Thr, Val, Arg, or an unnatural amino acid commonly used as a substitute thereof;

A9 is Phe, Leu, Ile, Tyr or an unnatural amino acid commonly used as a substitute thereof which includes cyclohexylalanine; and A10 is Cys, Ser, Ala, or an unnatural amino acid commonly used as a substitute thereof;

wherein the carboxy-terminal amino acid is in amide or carboxy-form;

wherein at least one sulfhydryl amino acid is present as one of the amino acids in the sequence; and wherein A1, A2, A3, A1 to A2, A1 to A3, A10, A9 to A10, A8 to A10, or a combination thereof are optionally absent, with the proviso that the peptide does not consist of amino acid residues 1 to 6 of Hep25.

In some embodiments, the peptides of the present invention are not Hep4-7, Hep3-7, Hep1-7, Hep9C7-tBut, Hep9-C7A, Hep9-7CS, (D)Pen, Cyc-2, Cyc-3, Cyc-4, or Pr26.

In some embodiments, the peptides of the present invention contain only one amino acid residue having a thiol capable of forming a disulfide bond.

In some embodiments, the peptides of the present invention contain only two amino acid residues which each have a thiol capable of forming a disulfide bond.

In some embodiments,

A1 is D-Asp, D-Glu, D-pyroglutamate, D-Gln, D-Asn, bhAsp, Ida, or N-MeAsp;

A2 is D-Thr, D-Ser, D-Val, Tle, Inp, Chg, bhThr, or N-MeThr;

A3 is D-His, D-Asn, DArg, Dpa, (D)Dpa, or 2-aminoindan;

A4 is D-Phe, D-Leu, D-Ile, D-Trp, Phg, bhPhe, Dpa, Bip, 1Nal, bhDpa, Amc, PheF5, hPhe, Igl, or cyclohexylalanine;

A5 is D-Pro, D-Ser, Oic, bhPro, trans-4-PhPro, cis-4-PhPro, cis-5-PhPro, Idc;

A6 is D-Ile, D-Leu, Phg, Chg, Amc, bhIle, Ach, and MeIle;

A7 is D-Cys, D-Ser, D-Ala, Cys(S-tBut), homoC, Pen, (D)Pen, Dap(AcBr), and Inp;

A8 is D-Ile, D-Leu, D-Thr, D-Val, D-Arg, Chg, Dpa, bhIle, Ach, or MeIle;

A9 is D-Phe, D-Leu, D-Ile, PheF5, N-MePhe, benzylamide, bhPhe, Dpa, Bip, 1Nal, bhDpa, cyclohexylalanine; or A10 is D-Cys, D-Ser, D-Ala;

or a combination thereof.

In some embodiments,

A1 is Ala, D-Ala, Cys, D-Cys, Phe, D-Phe, Asp or D-Asp linked to Cys or D-Cys, Phe or D-Phe linked to a PEG molecule linked to chenodeoxycholate, ursodeoxycholate, or palmitoyl, or Dpa or (D)Dpa linked to palmitoyl;

A2 is Ala, D-Ala, Cys, D-Cys, Pro, D-Pro, Gly, or D-Gly;

A3 is Ala, D-Ala, Cys, D-Cys, Dpa, Asp or D-Asp linked to Dpa or (D)Dpa;

A4 is Ala, D-Ala, Pro, or D-Pro;

A5 is Ala, D-Ala, Pro, D-Pro, Arg, D-Arg;

A6 is Ala, D-Ala, Phe, D-Phe, Arg, D-Arg, Cys, D-Cys;

A7 is His, or D-His;

A8 is Cys, or D-Cys; or

A9 is Phe or D-Phe linked to RA, Asp, D-Asp, Asp or D-Asp linked to RB, bhPhe linked to RC, or cysteamide, wherein RA is —CONH$_2$—CH$_2$—CH$_2$—S, -D-Pro linked to Pro-Lys or Pro-Arg, -bhPro linked to Pro linked to Pro-Lys or Pro-Arg, -D-Pro linked to bhPro-Lys or bhPro-Arg, wherein RB is -PEG11-GYIPEAPRDGQAYVRKDGEWVLLSTFL, -(PEG11)-(GPHyp)10, and wherein RC is -D-Pro linked to Pro-Lys or Pro-Arg, -D-Pro linked to bhPro-Lys or bhPro-Arg; or a combination thereof.

In some embodiments, A1 is Asp; A2 is Thr; A3 is His; A4 is Phe; A5 is Pro; A6 is Ile; A7 is Ala; A8 is Ile; A9 is Phe; and A10 is Cys in amide form; wherein A1 or A1 to A2 are optionally absent.

In some embodiments, A1 is Asp, A2 is Thr, A3 is His, A4 is Phe, A5 is Pro, A6 is Ile, A7 is Cys or an unnatural thiol amino acid, A8 is Ile, A9 is Phe in amide form, and A10 is absent.

In some embodiments, A1 and A2 are absent, A3 is His, A4 is Phe, A5 is Pro, A6 is Ile, A7 is Cys or an unnatural thiol amino acid, A8 is Ile in amide form, and A9 and A10 are absent.

In some embodiments, A1 and A2 are absent, A3 is His, A4 is Phe, A5 is Pro, A6 is Ile, A7 is Cys or an unnatural thiol amino acid in amide form, and A8 to A10 are absent.

In some embodiments, the peptides are cyclic peptides.

In some embodiments, the peptides are retroinverted such that A1 is the amidated C-terminus and A10 is the N-terminus, and all amino acids are D-amino acids instead of the natural L-amino acids.

In some embodiments, the peptides have an addition at the N-terminus, C-terminus, or both.

In some embodiments, the peptides are selected from the group consisting of: Hep3-8, Hep3-9, Hep1-8, Hep1-9, Hep1-10 C7A, Hep9F4A, Hep9C7-SStBut, (D)C, homoC, Pen, (D)Pen, Cyc-1, Pr10, Pr11, Pr12, riHep7ΔDT, Pr23, Pr24, Pr25, Pr27, Pr28, F4bhPhe, F4Dpa, F4Bip, F4 1Nal, F4bhDpa, F9bhPhe, F9Dpa, F9Bip, F91Nal, F9bhDpa, Pr39, Pr40, Pr41, Pr42, Pr43, Pr44, Pr45, Pr46, Pr13, Pr14, Pr15, Pr16, Pr17, Pr18, Pr19, Pr20, Pr21, Pr22, Pr-1, Pr-2, Pr-3, and Pr-4.

In some embodiments, the peptides exhibit hepcidin activity. In some embodiments, the peptides bind ferroportin, preferably human ferroportin.

In some embodiments, the present invention provides compositions and medicaments which comprise at least one peptide as disclosed herein. In some embodiments, the present invention provides method of manufacturing medicaments for the treatment of diseases of iron metabolism, such as iron overload diseases, which comprise at least one peptide as disclosed herein. Also provided are methods of treating a diseases of iron metabolism in a subject, such as a mammalian subject, preferably a human subject, which comprises administering at least one peptide or composition as disclosed herein to the subject. In some embodiments, the peptide is administered in a therapeutically effective amount.

In some embodiments, the present invention provides methods of binding a ferroportin or inducing ferroportin internalization and degradation which comprises contacting the ferroportin with at least one peptide or composition as disclosed herein.

In some embodiments, the present invention provides kits comprising at least one peptide or composition as disclosed herein packaged together with a reagent, a device, instructional material, or a combination thereof.

In some embodiments, the present invention provides complexes which comprise at least one peptide as disclosed herein bound to a ferroportin, preferably a human ferroportin, or an antibody, such as an antibody which specifically binds a peptide as disclosed herein, Hep25, or a combination thereof.

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description serve to explain the principles of the invention.

DESCRIPTION OF THE DRAWINGS

This invention is further understood by reference to the drawings wherein.

DETAILED DESCRIPTION OF THE INVENTION

Figure 1:
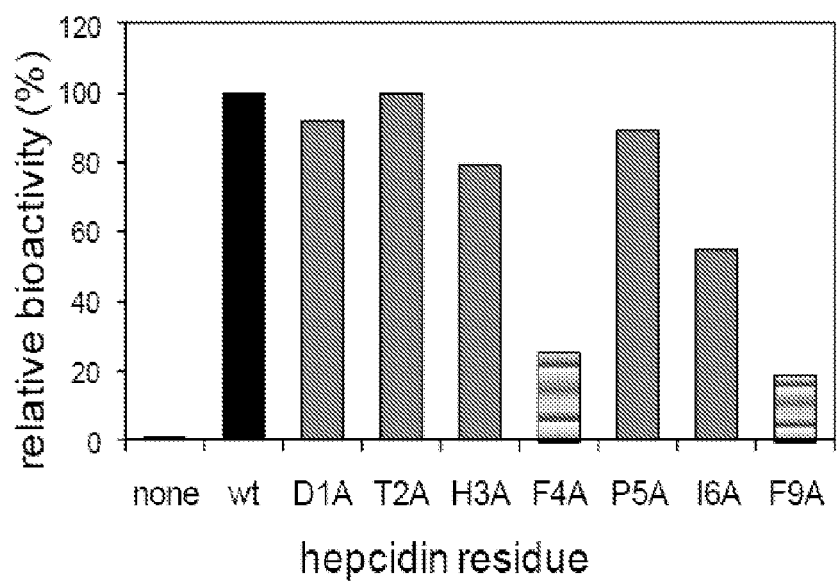
FIG. 1 is a graph showing the relative hepcidin activity of alanine substitutions in Hep25.

The present invention provides peptides which are useful in the study and treatment of diseases of iron metabolism.

As used herein, a "disease of iron metabolism" includes diseases where aberrant iron metabolism directly causes the disease, or where iron blood levels are dysregulated causing disease, or where iron dysregulation is a consequence of another disease, or where diseases can be treated by modulating iron levels, and the like. More specifically, a disease of iron metabolism according to this disclosure includes iron overload diseases, iron deficiency disorders, disorders of iron biodistribution, other disorders of iron metabolism and other disorders potentially related to iron metabolism, etc. Diseases of iron metabolism include hemochromatosis, HFE mutation hemochromatosis, ferroportin mutation hemochromatosis, transferrin receptor 2 mutation hemochromatosis, hemojuvelin mutation hemochromatosis, hepcidin mutation hemochromatosis, juvenile hemochromatosis, neonatal hemochromatosis, hepcidin deficiency, transfusional iron overload, thalassemia, thalassemia intermedia, alpha thalassemia, sideroblastic anemia, porphyria, porphyria cutanea tarda, African iron overload, hyperferritinemia, ceruloplasmin deficiency, atransferrinemia, congenital dyserythropoietic anemia, anemia of chronic disease, anemia of inflammation, anemia of infection, hypochromic microcytic anemia, iron-deficiency anemia, iron-refractory iron deficiency anemia, anemia of chronic kidney disease, erythropoietin resistance, iron deficiency of obesity, other anemias, benign or malignant tumors that overproduce hepcidin or induce its overproduction, conditions with hepcidin excess, Friedreich ataxia, gracile syndrome, Hallervorden-Spatz disease, Wilson's disease, pulmonary hemosiderosis, hepatocellular carcinoma, cancer, hepatitis, cirrhosis of liver, pica, chronic renal failure, insulin resistance, diabetes, atherosclerosis, neurodegenerative disorders, multiple sclerosis, Parkinson's disease, Huntington's disease, and Alzheimer's disease.

In some cases the diseases and disorders included in the definition of "disease of iron metabolism" are not typically identified as being iron related. For example, hepcidin is highly expressed in the murine pancreas suggesting that diabetes (Type I or Type II), insulin resistance, glucose intolerance and other disorders may be ameliorated by treating underlying iron metabolism disorders. See Ilyin, G. et al. (2003) FEBS Lett. 542 22-26, which is herein incorporated by reference. As such, these diseases are encompassed under the broad definition. Those skilled in the art are readily able to determine whether a given disease is a "disease or iron metabolism" according to the present invention using methods known in the art, including the assays of WO 2004092405, which is herein incorporated by reference, and assays which monitor hepcidin, hemojuvelin, or iron levels and expression, which are known in the art such as those described in U.S. Pat. No. 7,534,764, which is herein incorporated by reference.

In preferred embodiments of the present invention, the diseases of iron metabolism are iron overload diseases, which include hereditary hemochromatosis, iron-loading anemias, alcoholic liver diseases and chronic hepatitis C.

As used herein, the terms "protein", "polypeptide" and "peptide" are used interchangeably to refer to two or more amino acids linked together. Except for the abbreviations for the uncommon or unnatural amino acids set forth in Table 2 below, the three-letter and one-letter abbreviations, as used in the art, are used herein to represent amino acid residues. Except when preceded with "D-", the amino acid is an L-amino acid. Groups or strings of amino acid abbreviations are used to represent peptides. Except when specifically indicated, peptides are indicated with the N-terminus on the left and the sequence is written from the N-terminus to the C-terminus.

The peptides of the present invention may be made using methods known in the art including chemical synthesis, biosynthesis or in vitro synthesis using recombinant DNA methods, and solid phase synthesis. See e.g. Kelly & Winkler (1990) Genetic Engineering Principles and Methods, vol. 12, J. K. Setlow ed., Plenum Press, NY, pp. 1-19; Merrifield (1964) J Amer Chem Soc 85:2149; Houghten (1985) PNAS USA 82:5131-5135; and Stewart & Young (1984) Solid Phase Peptide Synthesis, 2ed. Pierce, Rockford, Ill., which are herein incorporated by reference. The peptides of the present invention may be purified using protein purification techniques known in the art such as reverse phase high-performance liquid chromatography (HPLC), ion-exchange or immunoaffinity chromatography, filtration or size exclusion, or electrophoresis. See Olsnes, S. and A. Pihl (1973) Biochem. 12(16):3121-3126; and Scopes (1982) Protein Purification, Springer-Verlag, NY, which are herein incorporated by reference. Alternatively, the peptides of the present invention may be made by recombinant DNA techniques known in the art. Thus, polynucleotides that encode the polypeptides of the present invention are contemplated herein. In preferred embodiments, the polynucleotides are isolated. As used herein "isolated polynucleotides" refers to polynucleotides that are in an environment different from that in which the polynucleotide naturally occurs.

In some embodiments, the peptides of the present invention are substantially purified. As used herein, a "substantially purified" compound refers to a compound that is removed from its natural environment and is at least about 60% free, preferably about 75% free, and most preferably about 90% free from other macromolecular components with which the compound is naturally associated.

As used herein, an "isolated" compound refers to a compound which is isolated from its native environment. For example, an isolated peptide is a one which does not have its native amino acids, which correspond to the full length polypeptide, flanking the N-terminus, C-terminus, or both. For example, isolated Hep1-9 refers to an isolated peptide comprising amino acid residues 1-9 of Hep25 which may have non-native amino acids at its N-terminus, C-terminus, or both, but does not have a cysteine amino acid residue following its $9^{th}$ amino acid residue at the C-terminus. As set forth herein, references to amino acid positions correspond to the amino acid residues of Hep25. For example, reference to amino acid position 9, corresponds to the $9^{th}$ amino acid residue of Hep25.

The peptides of the present invention bind ferroportin, preferably human ferroportin. Preferred peptides of the present invention specifically bind human ferroportin. As used herein, "specifically binds" refers to a specific binding agent's preferential interaction with a given ligand over other agents in a sample. For example, a specific binding agent that specifically binds a given ligand, binds the given ligand, under suitable conditions, in an amount or a degree that is observable over that of any nonspecific interaction with other components in the sample. Suitable conditions are those that allow interaction between a given specific binding agent and a given ligand. These conditions include pH, temperature, concentration, solvent, time of incubation, and the like, and may differ among given specific binding agent and ligand pairs, but may be readily determined by those skilled in the art.

The peptides of the present invention that mimic the hepcidin activity of Hep25, the bioactive human 25-amino acid form, are herein referred to as "mini-hepcidins". As used herein, a compound having "hepcidin activity" means that the compound has the ability to lower plasma iron concentrations in subjects (e.g. mice or humans), when administered thereto (e.g. parenterally injected or orally administered), in a dose-dependent and time-dependent manner. See e.g. as demonstrated in Rivera et al. (2005), Blood 106:2196-9.

In some embodiments, the peptides of the present invention have in vitro activity as assayed by the ability to cause the internalization and degradation of ferroportin in a ferroportin-expressing cell line as taught in Nemeth et al. (2006) Blood 107:328-33. In vitro activity may be measured by the dose-dependent loss of fluorescence of cells engineered to display ferroportin fused to green fluorescent protein as in Nemeth et al. (2006) Blood 107:328-33. Aliquots of cells are incubated for 24 hours with graded concentrations of a reference preparation of Hep25 or a mini-hepcidin. As provided herein, the $EC_{50}$ values are provided as the concentration of a given compound (e.g. peptide) that elicits 50% of the maximal loss of fluorescence generated by the reference Hep25 preparation. $EC_{50}$ of Hep25 preparations in this assay range from 5 to 15 nM and preferred mini-hepcidins have $EC_{50}$ values in in vitro activity assays of about 1,000 nM or less.

Other methods known in the art for calculating the hepcidin activity and in vitro activity of peptides according to the present invention may be used. For example, the in vitro activity of compounds may be measured by their ability to internalize cellular ferroportin, which is determined by immunohistochemistry or flow cytometry using antibodies which recognizes extracellular epitopes of ferroportin. Alternatively, the in vitro activity of compounds may be measured by their dose-dependent ability to inhibit the efflux of iron from ferroportin-expressing cells that are preloaded with radioisotopes or stable isotopes of iron, as in Nemeth et al. (2006) Blood 107:328-33.

Design of Mini-Hepcidins

Previous studies indicate that the N-terminal segment of Hep25 is important for its hepcidin activity and is likely to form the contact interface with ferroportin. However, the importance of each N-terminal amino acid to hepcidin activity was unknown. Therefore, alanine-scanning mutagenesis was performed on residues 1-6 of Hep25 to determine the contribution of each N-terminal amino acid to hepcidin activity. As shown in FIG. 1, the T2A substitution did not substantially impact hepcidin activity. Phenylalanine substitutions (F4A or F9A) caused the largest decrease, more than about 70%, in hepcidin activity. The remaining alanine substitutions had detectable decreases in hepcidin activity which were not as significant as the F4A or F9A substitutions.

Figure 2A:
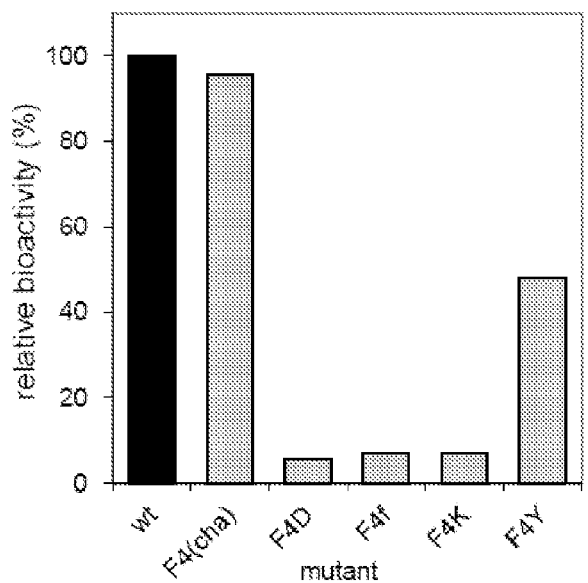
FIG. 2A is a graph showing the relative hepcidin activities of F4 substitutions in Hep25.

To determine whether the highly conserved and apparently structurally important F4 phenylalanine is important for hepcidin activity, the F4 amino acid of Hep25 was systematically substituted with other amino acids. As shown in FIG. 2A, making the side-chain more polar (F4Y) led to substantial loss of hepcidin activity as did the substitution with D-phenylalanine (f) or charged amino acids (D, K and Y). However, hepcidin activity was maintained when the F4 residue was substituted with nonaromatic cyclohexylalanine, thereby indicating that a bulky hydrophobic residue is sufficient for activity.

Figure 2B:
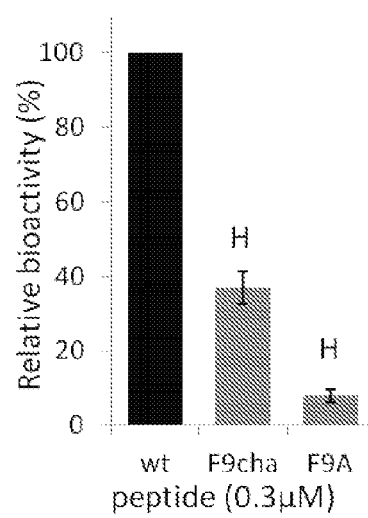
FIG. 2B is a graph showing the relative hepcidin activities of F9 substitutions in Hep25.

To determine whether the highly conserved and apparently structurally important F9 phenylalanine is important for hepcidin activity, the F9 amino acid of Hep25 was substituted with other amino acids. As shown in FIG. 2B, hepcidin activity not only decreased when F9 was substituted with alanine, but also when it was substituted with nonaromatic cyclohexylalanine, thereby indicating that an aromatic residue may be important for activity.

Mutational studies indicate that C326, the cysteine residue at position 326 of human ferroportin, is the critical residue involved in binding hepcidin. Thus, various N-terminal fragments of Hep25 containing a thiol, i.e. Hep 4-7, Hep3-7, Hep3-8, Hep3-9, Hep1-7, Hep1-8, Hep1-9, and Hep1-10 C7A, were chemically synthesized, refolded and their activities relative to Hep25 were assayed using flow-cytometric quantitation of the ferroportin-GFP degradation, iron efflux estimation based on measurements of cellular ferritin, and radioisotopic iron efflux studies. The sequences and $EC_{50}$'s of these N-terminal fragments are shown in Table 1.

Figure 3A:
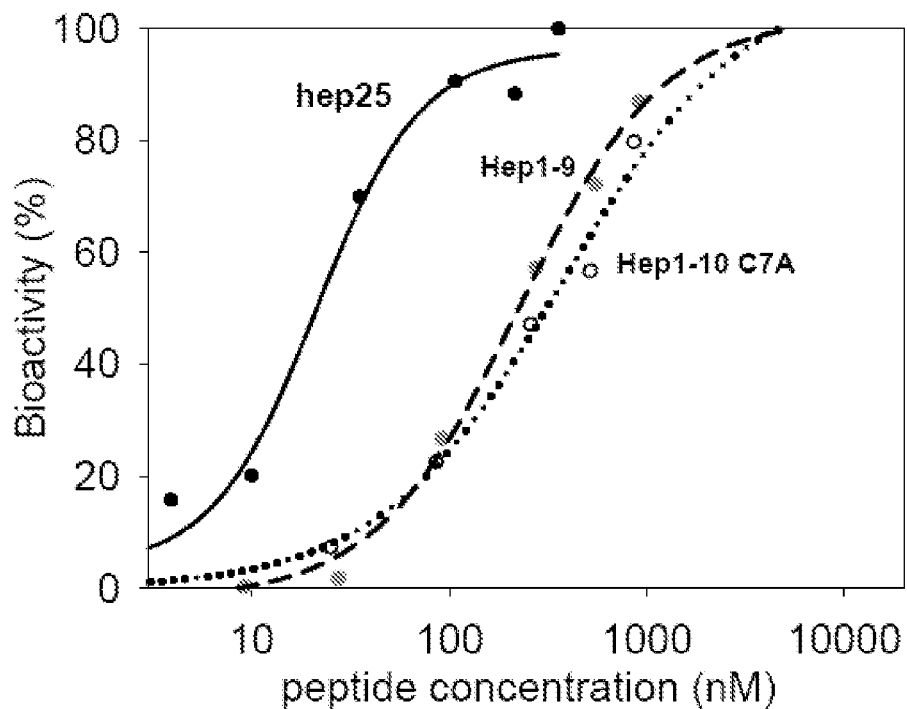
FIG. 3A is a graph showing the hepcidin activities of Hep1-9 and Hep1-10 C7A relative to Hep25 (A).
Figure 3B:
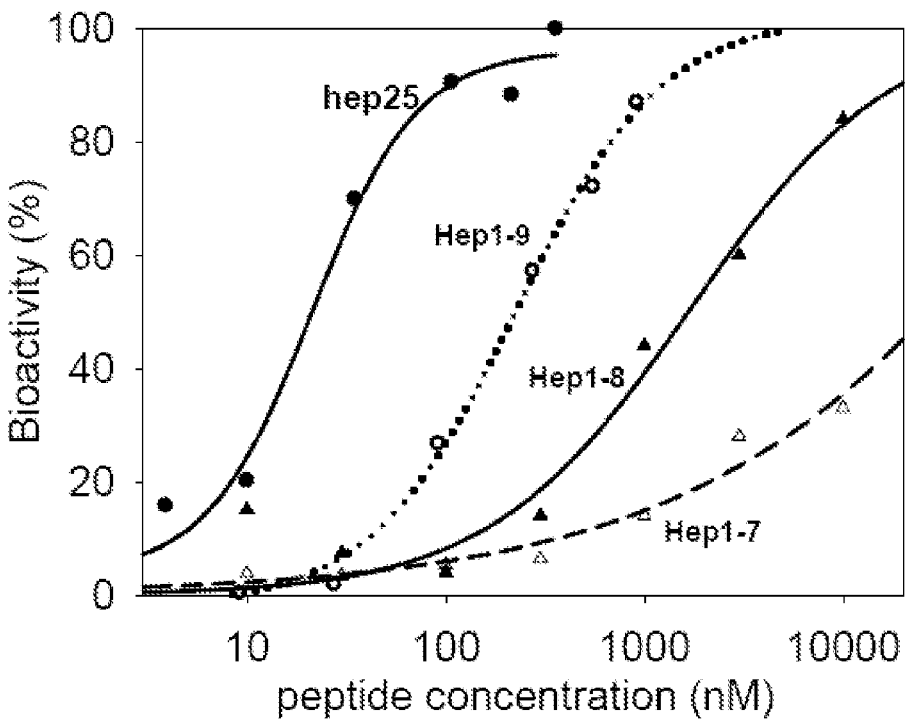
FIG. 3B is a graph showing the hepcidin activities of Hep1-7 and Hep1-8 relative to Hep1-9 or Hep25.
Figure 3C:
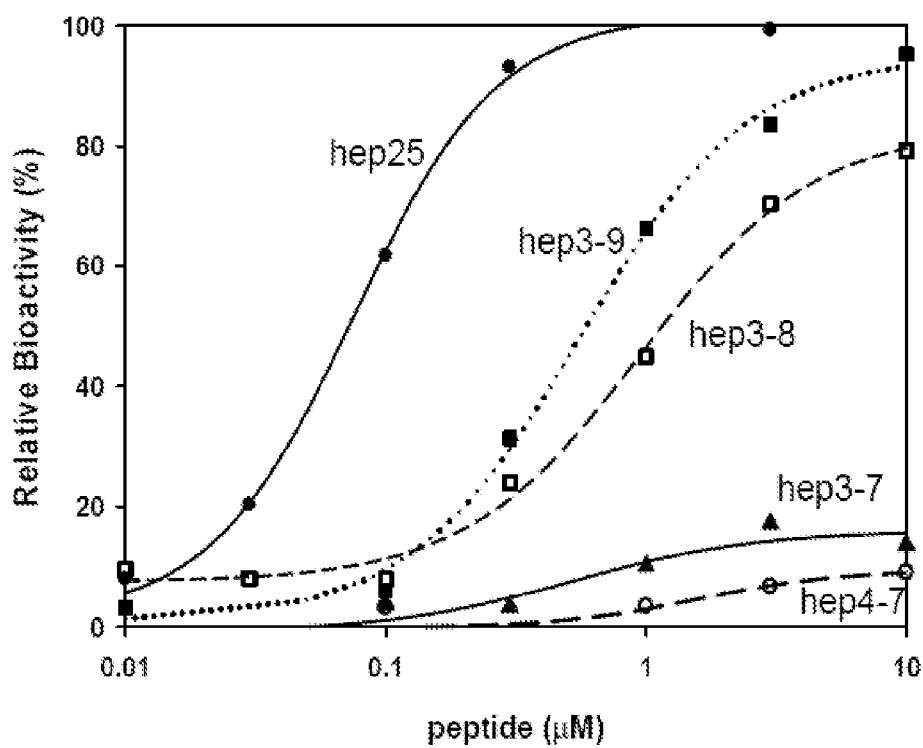
FIG. 3C is a graph showing the hepcidin activities of Hep4-7, Hep3-7, Hep3-8 and Hep3-9 relative to Hep1-9.

Remarkably and unexpectedly, as shown in FIG. 3, Hep1-9 and Hep1-10 C7A were found to be quite active in the flow-cytometry assay of ferroportin-GFP internalization. On a mass basis, Hep1-9 and Hep1-10 C7A were only about 4-times less potent and on a molar basis, about 10-times less potent than Hep25. Thus, Hep1-9 and Hep1-10 C7A were used as the basis to construct other peptides having hepcidin activity.

Figure 4:
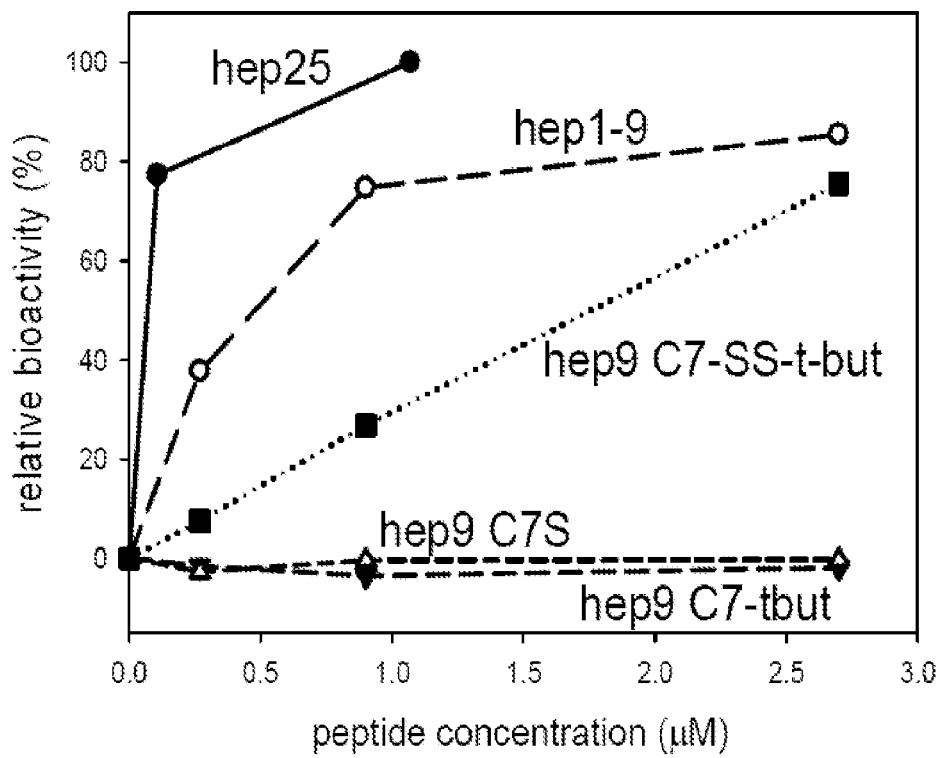
FIG. 4 is a graph showing the hepcidin activities of C7 modified peptides relative to Hep25.

To determine the importance of the cysteine thiol on the hepcidin activity of Hep1-9, the C7 residue of Hep1-9 was substituted with amino acids that have a similar shape but cannot form disulfide bonds to give Hep9-C7S (serine substitution) and Hep9C7-tBut (t-butyl-blocked cysteine) or with a cysteine modified by disulfide coupled tertiary butyl, which can participate in disulfide exchange with HS-t-butyl as the leaving group, to give Hep9C7-SStBut. As shown in FIG. 4, amino acid substitutions that ablated the potential for disulfide formation or exchange caused a complete loss of hepcidin activity, thereby indicating that disulfide formation is required for activity. Other C7 amino acid substitutions and their resulting hepcidin activities are shown in Table 1.

Other peptides based on Hep1-9 and Hep1-10 C7A were constructed to be disulfide cyclized, have unnatural amino acid substitutions, be retroinverted, have modified F4 and F9 residues, or have a positive charge. The C-terminal amino acid was the amidated form. The modifications and the resulting hepcidin activities are shown in Table 1.

As shown in Table 1, with the exception of Pr40 and Pr41, mini-hepcidins which exhibit $EC_{50}$'s of about 1000 nM or less contain at least 6 contiguous amino acid residues which correspond to residues 3-8 of Hep25 (see Hep3-8). Thus, in some embodiments, preferred mini-hepcidins have at least 6 contiguous amino acid residues that correspond to 6 contiguous amino acid residues of Hep1-9, preferably residues 3-8. The amino acid residues may be unnatural or uncommon amino acids, L- or D-amino acid residues, modified residues, or a combination thereof.

In some embodiments, the mini-hepcidins of the present invention have at least one amino acid substitution, a modification, or an addition. Examples of amino acid substitutions include substituting an L-amino acid residue for its corresponding D-amino acid residue, substituting a Cys for homoC, Pen, (D)Pen, Inp, or the like, substituting Phe for bhPhe, Dpa, bhDpa, Bip, 1Nal, and the like. The names and the structures of the substituting residues are exemplified in Table 2. Other suitable substitutions are exemplified in Table 1. Examples of a modification include modifying one or more amino acid residues such that the peptide forms a cyclic structure, retroinversion, and modifying a residue to be capable of forming a disulfide bond. Examples of an addition include adding at least one amino acid residue or at least one compound to either the N-terminus, the C-terminus, or both such as that exemplified in Table 1.

As shown in Table 1, a majority of the mini-hepcidins which exhibit $EC_{50}$'s of about 100 nM or less contain at least one Dpa or bhDPA amino acid substitution. Thus, in some embodiments, the mini-hepcidins of the present invention have at least one Dpa or bhDPA amino acid substitution.

In view of the alanine substitution data of FIG. 1, in some embodiments, the mini-hepcidins of the present invention may have an Ala at amino acid positions other than amino acid position 4 and 9 as long as there is an available thiol for forming a disulfide bond at amino acid position 7. See Hep9F4A and Hep9C-SStBut in Table 1.

In view of the position 4 amino acid substitution data of FIG. 2 and Table 1, the mini-hepcidins of the present invention may have an amino acid substitution at position 4 which does not result in a substantial change of its charge or polarity as compared to that of Hep25, Hep1-9 or Hep1-10 C7A. Preferred amino acid substitutions at position 4 of Hep1-9 or Hep1-10 C7A include Phe, D-Phe, bhPhe, Dpa, bhDpa, Bip, 1Nal, or the like.

The mini-hepcidins according to the present invention have the following structural formula

A1-A2-A3-A4-A5-A6-A7-A8-A9-A10 wherein
A1 is Asp, Glu, pyroglutamate, Gln, Asn, or an unnatural amino acid commonly used as a substitute thereof;
A2 is Thr, Ser, Val, Ala, or an unnatural amino acid commonly used as a substitute thereof;
A3 is His, Asn, Arg, or an unnatural amino acid commonly used as a substitute thereof;
A4 is Phe, Leu, Ile, Trp, Tyr, or an unnatural amino acid commonly used as a substitute thereof which includes cyclohexylalanine;
A5 is Pro, Ser, or an unnatural amino acid commonly used as a substitute thereof;
A6 is Ile, Leu, Val, or an unnatural amino acid commonly used as a substitute thereof;
A7 is Cys, Ser, Ala, or an unnatural amino acid commonly used as a substitute thereof which includes S-tertiary butyl-cysteine;
A8 is Ile, Leu, Thr, Val, Arg, or an unnatural amino acid commonly used as a substitute thereof;
A9 is Phe, Leu, Ile, Tyr, or an unnatural amino acid commonly used as a substitute thereof which includes cyclohexylalanine; and
A10 is Cys, Ser, Ala, or an unnatural amino acid commonly used as a substitute thereof;
wherein the carboxy-terminal amino acid is in amide or carboxy-form;
wherein a Cys or another sulfhydryl amino acid is present as one of the amino acids in the sequence; and
wherein A1, A2, A3, A1 to A2, A1 to A3, A10, A9 to A10, A8 to A10, or a combination thereof are optionally absent.

In some embodiments, A1 is Asp; A2 is Thr; A3 is His; A4 is Phe; A5 is Pro; A6 is Ile; A7 is Ala; A8 is Ile; A9 is Phe; and A10 is Cys in amide form; wherein A1 or A1 to A2 are optionally absent.

In some embodiments, A1 is Asp, A2 is Thr, A3 is His, A4 is Phe, A5 is Pro, A6 is Ile, A7 is Cys or an unnatural thiol amino acid, A8 is Ile, A9 is Phe in amide form, and A10 is absent.

In some embodiments, A1 and A2 are absent, A3 is His, A4 is Phe, A5 is Pro, A6 is Ile, A7 is Cys or an unnatural thiol amino acid, A8 is Ile in amide form, and A9 and A10 are absent.

In some embodiments, A1 and A2 are absent, A3 is His, A4 is Phe, A5 is Pro, A6 is Ile, A7 is Cys or an unnatural thiol amino acid in amide form, and A8 to A10 are absent.

In some embodiments, the unnatural amino acid of A1, A2, A3, A4, A5, A6, A7, A8, A9, A10, or a combination thereof is the corresponding D-amino acid. For example, for A1, the unnatural amino acid may be D-Asp, D-Glu, D-Gln, D-Asn, or the like.

In some embodiments, the unnatural amino acid for:
A1 is D-Asp, D-Glu, D-pyroglutamate, D-Gln, D-Asn, bhAsp, Ida, or N-MeAsp;
A2 is D-Thr, D-Ser, D-Val, Tle, Inp, Chg, bhThr, or N-MeThr;
A3 is D-His, D-Asn, DArg, Dpa, (D)Dpa, or 2-aminoindan;
A4 is D-Phe, D-Leu, D-Ile, D-Trp, Phg, bhPhe, Dpa, Bip, 1Nal, bhDpa, Amc, PheF5, hPhe, Igl, or cyclohexylalanine;
A5 is D-Pro, D-Ser, Oic, bhPro, trans-4-PhPro, cis-4-PhPro, cis-5-PhPro, Idc;
A6 is D-Ile, D-Leu, Phg, Chg, Amc, bhIle, Ach, and MeIle;
A7 is D-Cys, D-Ser, D-Ala, Cys(S-tBut), homoC, Pen, (D)Pen, Dap(AcBr), and Inp;
A8 is D-Ile, D-Leu, D-Thr, D-Val, D-Arg, Chg, Dpa, bhIle, Ach, or MeIle;
A9 is D-Phe, D-Leu, D-Ile, PheF5, N-MePhe, benzylamide, bhPhe, Dpa, Bip, 1Nal, bhDpa, cyclohexylalanine; and
A10 is D-Cys, D-Ser, D-Ala.

In some embodiments, the amino acid substitution (and addition, if indicated) for:
A1 is Ala, D-Ala, Cys, D-Cys, Phe, D-Phe, Asp or D-Asp linked to Cys or D-Cys, Phe or D-Phe linked to a PEG molecule linked to chenodeoxycholate, ursodeoxycholate, or palmitoyl, or Dpa or (D)Dpa linked to palmitoyl;
A2 is Ala, D-Ala, Cys, D-Cys, Pro, D-Pro, Gly, or D-Gly;
A3 is Ala, D-Ala, Cys, D-Cys, Dpa, Asp or D-Asp linked to Dpa or (D)Dpa;
A4 is Ala, D-Ala, Pro, or D-Pro;
A5 is Ala, D-Ala, Pro, D-Pro, Arg, D-Arg;
A6 is Ala, D-Ala, Phe, D-Phe, Arg, D-Arg, Cys, D-Cys;
A7 is His, or D-His;
A8 is Cys, or D-Cys; and
A9 is Phe or D-Phe linked to RA, Asp, D-Asp, Asp or D-Asp linked to RB, bhPhe linked to RC, or cysteamide, wherein RA is —CONH$_2$—CH$_2$—CH$_2$—S, -D-Pro linked to Pro-Lys or Pro-Arg, -bhPro linked to Pro linked to Pro-Lys or Pro-Arg, -D-Pro linked to bhPro-Lys or bhPro-Arg, wherein RB is -PEG11-GYIPEAPRDGQAYVRKDGEWVLLSTFL, -(PEG11)-(GPHyp)10, and wherein RC is -D-Pro linked to Pro-Lys or Pro-Arg, -D-Pro linked to bhPro-Lys or bhPro-Arg.

In some embodiments, the mini-hepcidin is a 10-mer sequence wherein A7 is Ala and A10 is Cys.

In some embodiments, the mini-hepcidin forms a cyclic structure by a disulfide bond.

In some embodiments, the mini-hepcidin is a retroinverted peptide such that A1 is the C-terminus and A10 is the N-terminus and the amino acid residues are D-amino acids. In some embodiments, the retroinverted peptide has at least one addition at the N-terminus, C-terminus, or both. In some embodiments, the retroinverted peptide contains at least one L-amino acid.

In some embodiments, the mini-hepcidin has an amino acid substitution at position 4, position 9, or both. In some embodiments, the amino acid substituent is Phg, Phe, D-Phe, bhPhe, Dpa, Bip, 1Nal, Dpa, bhDpa, Amc, or cysteamide.

In some embodiments, the mini-hepcidin has an amino acid substitution at position 7. In some embodiments, the amino acid substituent is Cys(S-tBut), Ala, D-Ala, Ser, D-Ser, homoC, Pen, (D)Pen, His, D-His, or Inp.

Examples of some preferred mini-hepcidins according to the present invention are provided in Table 1.

TABLE 1

| Name | 1 | 2 | 3 | 4 | 5 | 6 | 7 | 8 | 9 | 10 | EC$_{50}$ (nM) |
|---|---|---|---|---|---|---|---|---|---|---|---|
| Hep25 DTHFPICIFCCGCCHRSKCGMCCKT (SEQ ID NO: 1) | | | | | | | | | | | 10 |
| Hep10wt (SEQ ID NO: 2) | D | T | H | F | P | I | C | I | F | C | |
| *Length* | | | | | | | | | | | |
| Hep4 (Hep4-7) (SEQ ID NO: 3) | — | — | — | F | P | I | C | — | — | — | >10,000 |
| Hep5 (Hep3-7) (SEQ ID NO: 4) | — | — | H | F | P | I | C | — | — | — | >10,000 |
| Hep6 (Hep3-8) (SEQ ID NO: 5) | — | H | F | P | I | C | I | — | — | — | 1000 |
| Hep7ΔDT (Hep3-9) (SEQ ID NO: 6) | — | H | F | P | I | C | I | F | — | — | 700 |
| Hep7 (Hep1-7) (SEQ ID NO: 7) | D | T | H | F | P | I | C | — | — | — | >10,000 |
| Hep8 (Hep1-8) (SEQ ID NO: 8) | D | T | H | F | P | I | C | I | — | — | 2000 |
| Hep9 (Hep1-9) (SEQ ID NO: 9) | D | T | H | F | P | I | C | I | F | — | 76 |
| Hep10 (Hep1-10 C7A) (SEQ ID NO: 10) | D | T | H | F | P | I | A | I | F | C | 100 |
| *Thiol Modified* | | | | | | | | | | | |
| Hep9F4A (SEQ ID NO: 11) | D | T | H | A | P | I | C | I | F | — | >3000 |
| Hep9C7-SStBut | D | T | H | A | P | I | CS-S-tBut | I | F | — | 700 |
| Hep9C7-tBut | D | T | H | A | P | I | C-tBut | I | F | — | >10,000 |
| Hep9-C7A (SEQ ID NO: 12) | D | T | H | F | P | I | A | I | F | — | >10,000 |
| Hep9-C7S (SEQ ID NO: 13) | D | T | H | F | P | I | S | I | F | — | >10,000 |
| (D)C | D | T | H | F | P | I | <u>C</u> | I | F | — | 1000 |
| homoC | D | T | H | F | P | I | homoC | I | F | — | 900 |
| Pen | D | T | H | F | P | I | Pen | I | F | — | 700 |
| (D)Pen | D | T | H | F | P | I | <u>(D)Pen</u> | I | F | — | 3000 |
| Dap(AcBr) | D | T | H | F | P | I | Dap(AcBr) | I | F | — | >10000 |
| *Disulfide Cyclized* | | | | | | | | | | | |
| Cyc-1 (SEQ ID NO: 14) | <u>C</u>-D | T | H | F | P | I | <u>C</u> | I | F | — | 300 |
| Cyc-4 | D | T | H | F | P | I | <u>C</u> | I | F-R1 | — | >10000 |
| Cyc-2 (SEQ ID NO: 15) | — | <u>C</u> | H | F | P | I | <u>C</u> | I | F | — | >10000 |
| Cyc-3 | — | — | H | F | P | I | <u>C</u> | I | F-R1 | — | >10000 |
| *Unnatural AA's* | | | | | | | | | | | |
| Pr10 | D | Tle | H | Phg | Oic | Chg | C | Chg | F | — | >3000 |
| Pr11 | D | Tle | H | P | Oic | Chg | C | Chg | F | — | >3000 |
| *Retroinverted* | | | | | | | | | | | |
| Pr12 | <u>F</u> | <u>I</u> | <u>C</u> | <u>I</u> | <u>P</u> | <u>F</u> | <u>H</u> | <u>T</u> | <u>D</u> | — | 900* |
| riHep7ΔDT | <u>F</u> | <u>I</u> | <u>C</u> | <u>I</u> | <u>P</u> | <u>F</u> | <u>H</u> | — | — | — | 150* |
| *Modified Retroinverted* | | | | | | | | | | | |
| Pr23 | R2-<u>F</u> | <u>I</u> | <u>C</u> | <u>I</u> | <u>P</u> | <u>F</u> | <u>H</u> | <u>T</u> | <u>D</u> | — | 100 |
| Pr24 | R3-<u>F</u> | <u>I</u> | <u>C</u> | <u>I</u> | <u>P</u> | <u>F</u> | <u>H</u> | <u>T</u> | <u>D</u> | — | 1000* |
| Pr25 | F | <u>I</u> | <u>C</u> | <u>I</u> | <u>P</u> | <u>F</u> | <u>H</u> | <u>T</u> | <u>D</u>-R6 | — | 600 |
| Pr26 | F | <u>I</u> | <u>C</u> | <u>I</u> | <u>P</u> | <u>F</u> | <u>H</u> | <u>T</u> | <u>D</u>-R7 | — | >10,000 |
| Pr27 | R4-<u>F</u> | <u>I</u> | <u>C</u> | <u>I</u> | <u>P</u> | <u>F</u> | <u>H</u> | <u>T</u> | <u>D</u> | — | 20* |
| Pr28 | R5-<u>F</u> | <u>I</u> | <u>C</u> | <u>I</u> | <u>P</u> | <u>F</u> | <u>H</u> | <u>T</u> | <u>D</u> | — | 3000 |

TABLE 1-continued

| Name | 1 | 2 | 3 | 4 | 5 | 6 | 7 | 8 | 9 | 10 | $EC_{50}$ (nM) |
|---|---|---|---|---|---|---|---|---|---|---|---|
| Modified F4 and F9 | | | | | | | | | | | |
| F4bhPhe | D | T | H | bhPhe | P | I | C | I | F | — | 700 |
| F4Dpa | D | T | H | Dpa | P | I | C | I | F | — | 30 |
| F4Bip | D | T | H | Bip | P | I | C | I | F | — | 150 |
| F4 1Nal | D | T | H | 1Nal | P | I | C | I | F | — | 110 |
| F4bhDpa | D | T | H | bhDpa | P | I | C | I | F | — | 80 |
| F9bhPhe | D | T | H | F | P | I | C | I | bhPhe | — | 150 |
| F9Dpa | D | T | H | F | P | I | C | I | Dpa | — | 70 |
| F9Bip | D | T | H | F | P | I | C | I | Bip | — | 150 |
| F91Nal | D | T | H | F | P | I | C | I | 1Nal | — | 200 |
| F9bhDpa | D | T | H | F | P | I | C | I | bhDpa | — | 100 |
| Pr39 | D | T | H | Dpa | P | I | C | I | Dpa | — | 35 |
| Pr40 | D | — | Dpa | — | P | I | C | I | F | — | 70 |
| Pr41 | D | — | Dpa | — | P | I | C | I | Dpa | — | 300 |
| Pr42 | D | T | H | Dpa | P | <u>R</u> | C | <u>R</u> | Dpa | — | 30 |
| Pr43 | D | T | H | Dpa | P | <u>R</u> | C | <u>R</u> | Dpa | — | 200 |
| Pr44 | D | T | H | Dpa | Oic | I | C | I | F | — | 30 |
| Pr45 | D | T | H | Dpa | Oic | I | C | I | Dpa | — | 150 |
| Pr46 | D | T | H | Dpa | P | C | C | C | Dpa | — | 80 |
| Positive Charge | | | | | | | | | | | |
| Pr13 | D | T | H | F | P | I | C | I | F-R8 | — | 100 |
| Pr14 | D | T | H | F | P | I | C | I | F-R9 | — | 90 |
| Pr15 | D | T | H | F | P | I | C | I | F-R10 | — | 150 |
| Pr16 | D | T | H | F | P | I | C | I | F-R11 | — | 50 |
| Pr17 | D | T | H | F | P | I | C | I | F-R12 | — | 300 |
| Pr18 | D | T | H | F | P | I | C | I | F-R13 | — | 1000 |
| Pr19 | D | T | H | F | P | I | C | I | bhPhe-R8 | — | 700 |
| Pr20 | D | T | H | F | P | I | C | I | bhPhe-R9 | — | 200 |
| Pr21 | D | T | H | F | P | I | C | I | bhPhe-R12 | — | 500 |
| Pr22 | D | T | H | F | P | I | C | I | bhPhe-R13 | — | 600 |
| Pr-1 | C | Inp | <u>(D)Dpa</u> | Amc | R | Amc | Inp | Dpa | Cysteamide** | — | 1500 |
| Pr-2 | C | P | <u>(D)Dpa</u> | Amc | R | Amc | Inp | Dpa | Cysteamide** | — | 2000 |
| Pr-3 | C | <u>P</u> | <u>(D)Dpa</u> | Amc | R | Amc | Inp | Dpa | Cysteamide** | — | 1000 |
| Pr-4 | C | G | <u>(D)Dpa</u> | Amc | R | Amc | Inp | Dpa | Cysteamide** | — | 2000 |

R1 = —CONH$_2$—CH$_2$—CH$_2$—<u>S</u>
R2 = Chenodeoxycholate-(PEG11)-
R3 = Ursodeoxycholate-(PEG11)-
R4 = Palmitoyl-(PEG11)-
R5 = 2(Palmitoyl)-Dap(PEG11)-, wherein "Dap" = diaminopropionic acid
R6 = -PEG11-GYIPEAPRDGQAYVRKDGEWVLLSTFL
R7 = -(PEG11)-(GPHyp)10, "GPHyp" = Gly-Pro-hydroxyproline
R8 = -<u>PP</u>K
R9 = -<u>PP</u>R
R10 = -bhProPK
R11 = -bhProPR
R12 = -<u>P</u>bhProK
R13 = -<u>P</u>bhProR
Underlined residues = D amino acids
"—" indicates a covalent bond, e.g. point of attachment to the given peptide
Double underlined = residues connected by a disulfide link to form a cyclized structure
*active in vivo
**oxidized
The PEG compound may be PEG11, i.e. O-(2-aminoethyl)-O'-(2-carboxyethyl)-undecaethyleneglycol

TABLE 2

Uncommon or Unnatural Amino Acids

Chg

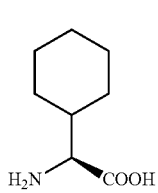

L-α-cyclohexylglycine

TABLE 2-continued

Uncommon or Unnatural Amino Acids

Tle

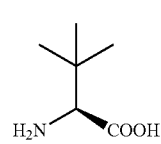

L-tert-leucine

TABLE 2-continued

Uncommon or Unnatural Amino Acids bhPhe

β-homophenylalanine
Dpa 3,3-diphenyl-L-alanine
bhPro

L-β-homoproline
Phg

L-phenylglycine
1Nal (1-naphthyl)-L-alanine
bhDpa (S)-3-Amino-4,4-
diphenylbutanoic acid TABLE 2-continued Uncommon or Unnatural Amino Acids Bip L-biphenylalanine
Pen L-Penicillamine
(D)Pen D-Penicillamine
Cys(tBut)

S-t-butyl-L-cysteine
Oic octahydroindole-2-
carboxylic acid
Dap(AcBr)

$N^Y$-(bromoacetyl)-L-2,3-
diaminopropionic acid

TABLE 2-continued

Uncommon or Unnatural Amino Acids

HomoC

L-homocysteine
Cys(S-tBut)

S-t-Butylthio-L-cysteine
Amc 4-(aminomethyl)cyclohexane carboxylic acid
Inp isonipecotic acid
bhAsp Ida N-MeAsp TABLE 2-continued Uncommon or Unnatural Amino Acids N-MeThr 2-Aminoindan PheF5 hPhe

Igl trans-4-PhPro

TABLE 2-continued

| Uncommon or Unnatural Amino Acids |
|---|
| cis-4-PhPro 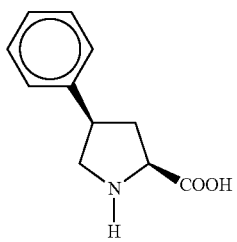 |
| cis-5-PhPro 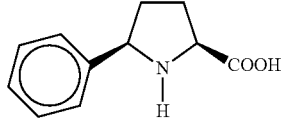 |
| Idc 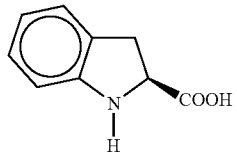 |
| bhIle 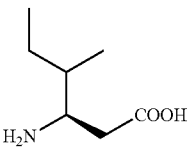 |
| Ach  |
| N-MeIle 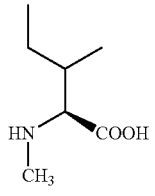 |
| N-MePhe 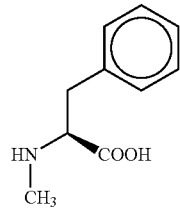 |

TABLE 2-continued

| Uncommon or Unnatural Amino Acids |
|---|
| Benzylamide 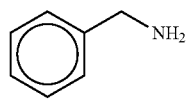 |
| (D)Dpa 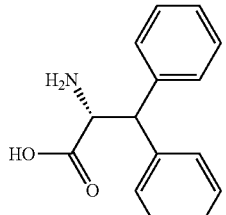 |
| 3,3-diphenyl-D-alanine |

In some embodiments, one or more peptides as described herein, are provided in the form of a composition which comprises a carrier suitable for its intended purpose. The compositions may also include one or more additional ingredients suitable for its intended purpose. For example, for assays, the compositions may comprise liposomes, niclosamide, SL220 solubilization agent (NOF, Japan), cremophor EL (Sigma), ethanol, and DMSO. For treatment of an iron overload disease, the compositions may comprise different absorption enhancers and protease inhibitors, solid microparticles or nanoparticles for peptide encapsulation (such as chitosan and hydrogels), macromolecular conjugation, lipidization and other chemical modification.

The present invention also provides kits comprising one or more peptides and/or compositions of the present invention packaged together with reagents, devices, instructional material, or a combination thereof. For example, the kits may include reagents used for conducting assays, drugs and compositions for diagnosing, treating, or monitoring disorders of iron metabolism, devices for obtaining samples to be assayed, devices for mixing reagents and conducting assays, and the like.

As the peptides of the present invention exhibit hepcidin activity, i.e. act as agonists of ferroportin degradation, they may be used to treat iron overload diseases. For example, one or more peptides (preferably at least one mini-hepcidin) according to the present invention may be administered to a subject to ameliorate the symptoms and/or pathology associated with iron overload in iron-loading anemias (especially β-thalassemias) where phlebotomy is contraindicated and iron chelators are the mainstay of treatment but are often poorly tolerated. One or more peptides, preferably at least one mini-hepcidin, according to the present invention may be used to treat hereditary hemochromatosis, especially in subjects who do not tolerate maintenance phlebotomy. One or more peptides, preferably at least one mini-hepcidin, according to the present invention may be used to treat acute iron toxicity.

Thus, one or more peptides of the present invention may be administered to a subject, preferably a mammal such as a human. In some embodiments, the peptides are administered in a form of a pharmaceutical composition. In some embodiments, the peptides are administered in a therapeutically effective amount. As used herein, a "therapeutically effective amount" is an amount which ameliorates the symptoms and/or pathology of a given disease of iron metabolism as compared to a control such as a placebo.

A therapeutically effective amount may be readily determined by standard methods known in the art. The dosages to be administered can be determined by one of ordinary skill in the art depending on the clinical severity of the disease, the age and weight of the subject, or the exposure of the subject to iron. Preferred effective amounts of the compounds of the invention ranges from about 0.01 to about 10 mg/kg body weight, preferably about 0.1 to about 3 mg/kg body weight, and more preferably about 0.5 to about 2 mg/kg body weight for parenteral formulations. Preferred effective amounts for oral administration would be up to about 10-fold higher. Moreover, treatment of a subject with a peptide or composition of the present invention can include a single treatment or, preferably, can include a series of treatments. It will be appreciated that the actual dosages will vary according to the particular peptide or composition, the particular formulation, the mode of administration, and the particular site, host, and disease being treated. It will also be appreciated that the effective dosage used for treatment may increase or decrease over the course of a particular treatment. Optimal dosages for a given set of conditions may be ascertained by those skilled in the art using conventional dosage-determination tests in view of the experimental data for a given peptide or composition. Changes in dosage may result and become apparent by standard diagnostic assays known in the art. In some conditions chronic administration may be required.

The pharmaceutical compositions of the invention may be prepared in a unit-dosage form appropriate for the desired mode of administration. The compositions of the present invention may be administered for therapy by any suitable route including oral, rectal, nasal, topical (including buccal and sublingual), vaginal and parenteral (including subcutaneous, intramuscular, intravenous and intradermal). It will be appreciated that the preferred route will vary with the condition and age of the recipient, the nature of the condition to be treated, and the chosen peptide and composition.

Pharmaceutical compositions of the present invention comprise a therapeutically effective amount of at least one peptide as disclosed herein, and an inert, pharmaceutically acceptable carrier or diluent. As used herein the language "pharmaceutically acceptable carrier" is intended to include any and all solvents, dispersion media, coatings, antibacterial and antifungal agents, isotonic and absorption delaying agents, and the like, compatible with pharmaceutical administration and known in the art. Except insofar as any conventional media or agent is incompatible with the active compound, use thereof in the compositions is contemplated.

Supplementary active compounds can also be incorporated into the compositions. Supplementary active compounds include niclosamide, liposomes, SL220 solubilization agent (NOF, Japan), cremophor EL (Sigma), ethanol, and DMSO.

Toxicity and therapeutic efficacy of the peptides and compositions of the present invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Peptides which exhibit large therapeutic indices are preferred. While peptides that exhibit toxic side effects may be used, care should be taken to design a delivery system that targets such peptides to the site of affected tissue in order to minimize potential damage to uninfected cells and, thereby, reduce side effects.

The data obtained from the cell culture assays and animal studies can be used in formulating a range of dosage for use in humans. The dosage of peptides of the present invention lies preferably within a range of circulating concentrations that include the $ED_{50}$ with little or no toxicity. The dosage may vary within this range depending upon the dosage form employed and the route of administration utilized. For any peptide used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Peptide Synthesis

Hep25 was synthesized at the UCLA Peptide Synthesis Core Facility using solid phase 9-fluorenylmethyloxycarbonyl (fmoc) chemistry. Specifically, the peptides were synthesized on an ABI 431A peptide synthesizer (PE Biosystems, Applied Biosystems, Foster City, Calif.) using fmoc amino acids, Wang resin (AnaSpec, San Jose, Calif.), and double coupling for all residues. After cleavage, 30 mg crude peptides was reduced with 1000-fold molar excess of dithiothreitol (DTT) in 0.5 M Tris buffer (pH 8.2), 6 M guanidine hydrochloride, and 20 mM EDTA at 52° C. for 2 hours. Fresh DTT (500-molar excess) was added and incubated for an additional hour at 52° C. The reduced peptides were purified on the 10-g C18 SEP-PAK cartridges (Waters, Milford, Mass.) equilibrated in 0.1% TFA and eluted with 50% acetonitrile. The eluates were lyophilized and resuspended in 0.1% acetic acid. The reduced peptides were further purified by reversed-phase high-performance liquid chromatography (RP-HPLC) on VYDAC C18 column (218TP510; Waters) equilibrated with 0.1% trifluoroacetic acid and eluted with an acetonitrile gradient. The eluates were lyophilized, dissolved in 0.1% acetic acid, 20% DMSO, to the approximate concentration of 0.1 mg/ml (pH 8), and air oxidized by stirring for 18 hours at room temperature. The refolded peptides were also purified sequentially on the 10-g C18 SEP-PAK cartridge and on the RP-HPLC VYDAC C18 column using an acetonitrile gradient. The eluates were lyophilized and resuspended in 0.016% HCl. The conformation of refolded synthetic hepcidin derivatives was verified by electrophoresis in 12.5% acid-urea polyacrylamide gel electrophoresis (PAGE), and peptide masses were determined by matrix-assisted laser desorption/ionization time-of-flight mass spectrometry (MALDI-TOF-MS; UCLA Mass Spectrometry Facility, Los Angeles, Calif.).

The other peptides set forth in Table 1 were synthesized by the solid phase method using either Symphony® automated peptide synthesizer (Protein Technologies Inc., Tucson, Ariz.) or CEM Liberty automatic microwave peptide synthesizer (CEM Corporation Inc., Matthews, N.C.), applying 9-fluorenylmethyloxycarbonyl (Fmoc) chemistry (Fields & Noble (1990) Int J Pept Protein Res 35:161-214) and commercially available amino acid derivatives and reagents (EMD Biosciences, San Diego, Calif. and Chem-Impex International, Inc., Wood Dale, Ill.). Peptides were cleaved from resin using modified reagent K (TFA 94% (v/v); phenol, 2% (w/v); water, 2% (v/v); TIS, 2% (v/v); 2 hours) and precipitated by addition of ice-cold diethyl ether. Subsequently, peptides were purified by preparative reverse-phase high performance liquid chromatography (RP-HPLC) to >95% homogeneity and their purity evaluated by matrix-assisted laser desorption ionization spectrometry (MALDI-MS, UCLA Mass Spectrometry Facility, Los Angeles, Calif.) as well as analytical RP-HPLC employing Varian ProStar 210 HPLC system equipped with ProStar 325 Dual Wavelength UV-Vis detector with the wavelengths set at 220 nm and 280 nm (Varian Inc., Palo Alto, Calif.). Mobile phases consisted of solvent A, 0.1% TFA in water, and solvent B, 0.1% TFA in acetonitrile. Analyses of peptides were performed with a reversed-phase C18 column (Vydac 218TP54, 4.6×250 mm, Grace, Deerfield, Ill.) applying linear gradient of solvent B from 0 to 100% over 100 min (flow rate: 1 ml/min).

Other methods known in the art may be used to synthesize or obtain the peptides according to the present invention. All peptides were synthesized as carboxyamides ($-CONH_2$) which creates a charge-neutral end more similar to a peptide bond than the negatively charged —COOH end. Nevertheless, peptides having the negatively charged —COOH end are contemplated herein.

Activity Assays

FLOW CYTOMETRY. The activity of peptides of the present invention was measured by flow cytometry as previously described. See Nemeth et al. (2006) Blood 107:328-333, which is herein incorporated by reference. ECR293/Fpn-GFP, a cell line stably transfected with a ponasterone-inducible ferroportin construct tagged at the C-terminus with green fluorescent protein was used. See Nemeth et al. (2004) Science 306:2090-2093, which is herein incorporated by reference. Briefly, the cells were plated on poly-D-lysine coated plates in the presence of 20 µM FAC, with or without 10 µM ponasterone. After 24 hours, ponasterone was washed off, and cells were treated with peptides for 24 hours. Cells were then trypsinized and resuspended at $1 \times 10^6$ cells/ml, and the intensity of green fluorescence was analyzed by flow cytometry. Flow cytometry was performed on FACSCAN (fluorescence activated cell scanner) Analytic Flow Cytometer (Becton Dickinson, San Jose, Calif.) with CELLQUEST version 3.3 software (Becton Dickinson). Cells not induced with ponasterone to express Fpn-GFP were used to establish a gate to exclude background fluorescence. Cells induced with ponasterone, but not treated with any peptides, were used as the positive control. Each peptide was tested over the range of concentrations (0, 0.01, 0.03, 0.1, 0.3, 1, 3 and 10 µM). Each peptide treatment was repeated independently 3 to 6 times. For each concentration of peptide, the results were expressed as a fraction of the maximal activity ($F_{Hep25}$) of Hep25 (in the dose range 0.01-10 µM), according to the formula $1-((F_x-F_{Hep25})/(F_{untreated}-F_{Hep25}))$, where F was the mean of the gated green fluorescence and x was the peptide. The $IEC_{50}$ concentrations are set forth in the Table 1.

FERRITIN ASSAY. Cells treated with peptides having hepcidin activity will retain iron and contain higher amounts of ferritin. Thus, following ferritin assay may be used to identify mini-hepcidins according to the present invention. Briefly, HEK293-Fpn cells are incubated with 20 µM FAC with or without 10 µM ponasterone. After 24 hours, ponasterone is washed off, and hepcidin derivatives are added for 24 hours in the presence of 20 µM FAC. Cellular protein is extracted with 150 mM NaCl, 10 mM EDTA, 10 mM Tris (pH 7.4), 1% Triton X-100, and a protease inhibitor cocktail (Sigma-Aldrich, St Louis, Mo.). Ferritin levels are determined by an enzyme-linked immunosorbent assay (ELISA) assay (Ramco Laboratories, Stafford, Tex., or Biotech Diagnostic, Laguna Niguel, Calif.) according to the manufacturer's instructions and are normalized for the total protein concentration in each sample, as determined by the bicinchoninic acid (BCA) assay (Pierce, Rockford, Ill.).

IN VIVO ASSAYS. Serum iron assay. The decrease in serum iron after peptide administration is the principal measure of hepcidin activity. Thus, as provided herein, the hepcidin activity of selected peptides of the present invention were assayed in vivo by measuring serum iron in test subjects. Briefly, C57/Bl6J mice were maintained on NIH 31 rodent diet (333 parts per million (ppm) iron; Harlan Teklad, Indianapolis, Ind.). Two weeks before the experiment, the mice were switched to a diet containing about 2-4 ppm iron (Harlan Teklad, Indianapolis, Ind.) in order to suppress endogenous hepcidin. Peptide stocks were diluted to desired concentrations in sterile phosphate buffered saline (PBS) or other diluents as described next. Mice were subjected to the following treatments: (a) Injected intraperitoneally either with 100 µl PBS (control) or with 50 µg peptide in 100 µl PBS; (b) Injected with 100 µl of peptide (or PBS) mixed with 500 µg empty liposomes COATSOME EL series (NOF, Tokyo, Japan) (prepared as per manufacturer's recommendation); (c) Injected with 100 µl peptides (or PBS) solubilized with SL220 solubilization agent (NOF, Tokyo, Japan); (d) Gavaged with 250 µl of peptide (or PBS) in 1× solvent (Cremophor EL (Sigma)/ethanol/PBS; (12.5:12.5:75)). Mice were sacrificed 4 hours later, blood was collected by cardiac puncture, and serum was separated using MICROTAINER tubes (Becton Dickinson, Franklin Lakes, N.J.). Serum iron was determined by using a colorimetric assay (Diagnostic Chemicals, Oxford, Conn.), which was modified for the microplate format so that 10 µl serum was used per measurement. The results were expressed as the percentage of decrease in serum iron when compared with the average value of serum iron levels in PBS-treated mice.

Figure 5:
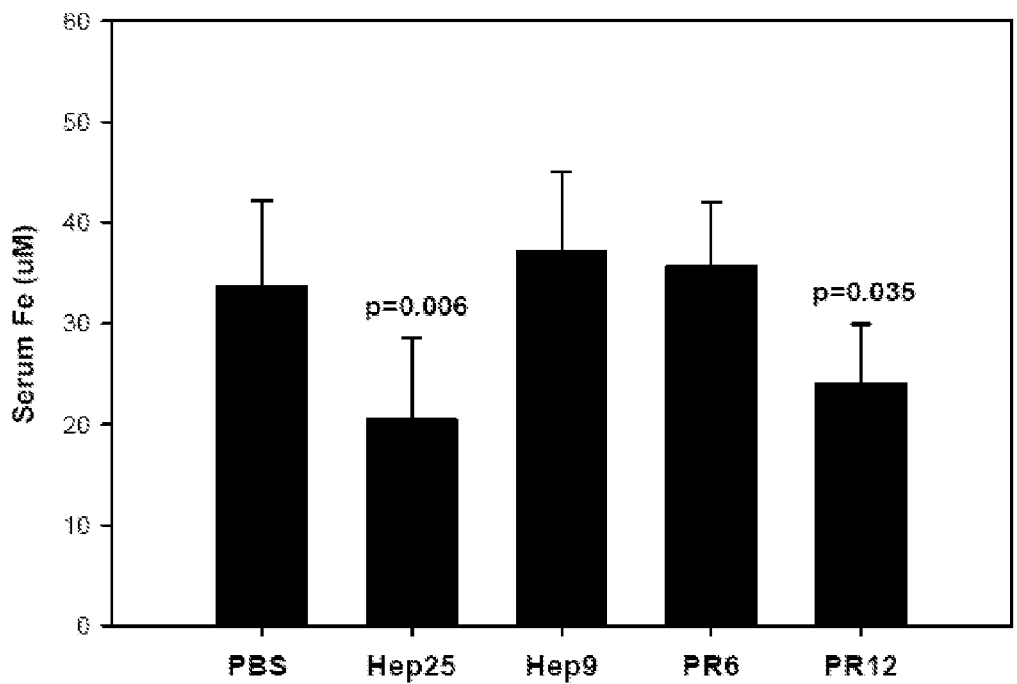
FIG. 5 is a graph showing in vivo effect (as measured by serum iron levels in mice) of mini-hepcidins Hep1-9, Pr6 and Pr12 compared to Hep25 or control (PBS). The peptides were injected intraperitoneally, 50 μg peptide per mouse

As shown in FIG. 5, intraperitoneal (i.p.) administration of 50 µg Pr12 per mouse in PBS caused a significant decrease in serum iron after 4 hours, when compared to i.p. administration of PBS. The serum iron decrease was similar to that caused by i.p. injection of 50 µg of Hep25. Injection (i.p.) of Hep9 did not result in a serum iron decrease. Pr12 is a retro-inverted form of Hep9, and is resistant to proteolysis because of the retroinverted structure. The experiment indicates that increased proteolytic resistance improves the activity of mini-hepcidins.

Figure 6:
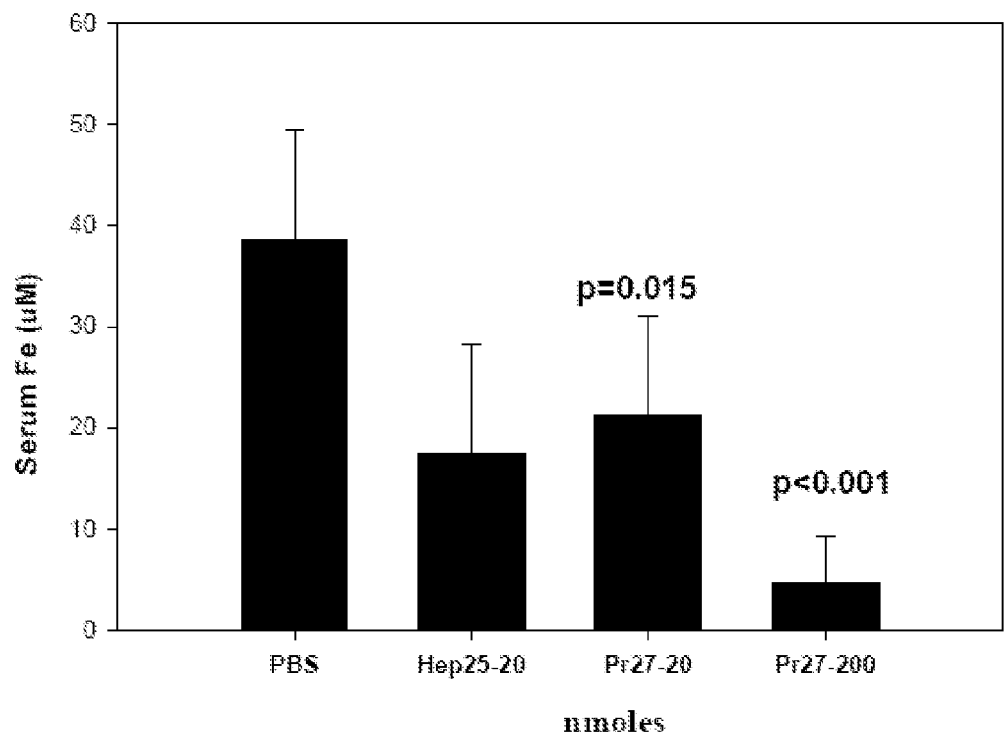
FIG. 6 is a graph showing in vivo effect (as measured by serum iron levels in mice) of mini-hepcidin Pr27 injected intraperitoneally (20 and 200 nmoles). The amount of injected Hep25 was 20 nmoles.

As shown in FIG. 6, i.p. administration of 200 nmoles of riHep7ΔDT in PBS resulted in serum iron concentrations significantly lower than those achieved after injection of PBS, and also lower than i.p. injection of 20 nmoles of Hep25. Administration of 20 nmoles of riHep7ΔDT slightly but not significantly reduced serum iron concentrations. The experiment indicates that after i.p. injection peptides as small as 7 amino acids are able to display activity comparable to Hep25.

Figure 7:
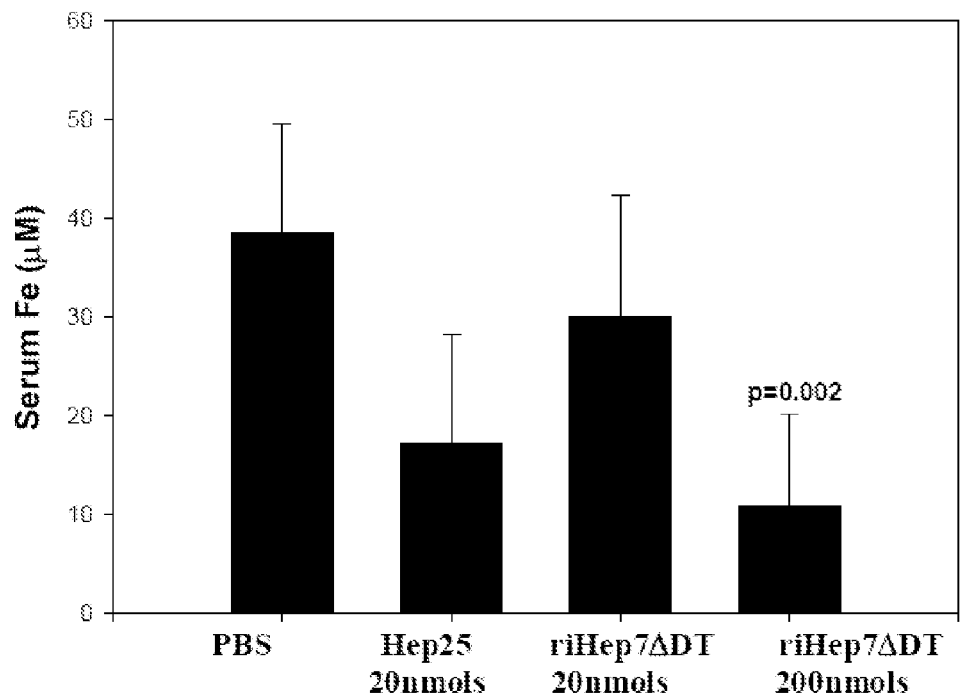
FIG. 7 is a graph showing in vivo effect (as measured by serum iron levels in mice) of mini-hepcidin riHep7ΔDT injected intraperitoneally (20 and 200 nmoles). The amount of injected Hep25 was 20 nmoles.

As shown in FIG. 7, i.p. administration of 20 nmoles Pr27 in PBS caused a serum iron decrease comparable to that caused by i.p. administration of 20 nmoles Hep25. This indicated that mini-hepcidin can achieve similar potency to Hep25 in vivo. Higher concentration of Pr27 (200 nmoles) caused even greater decrease in serum iron concentrations.

Figure 8:
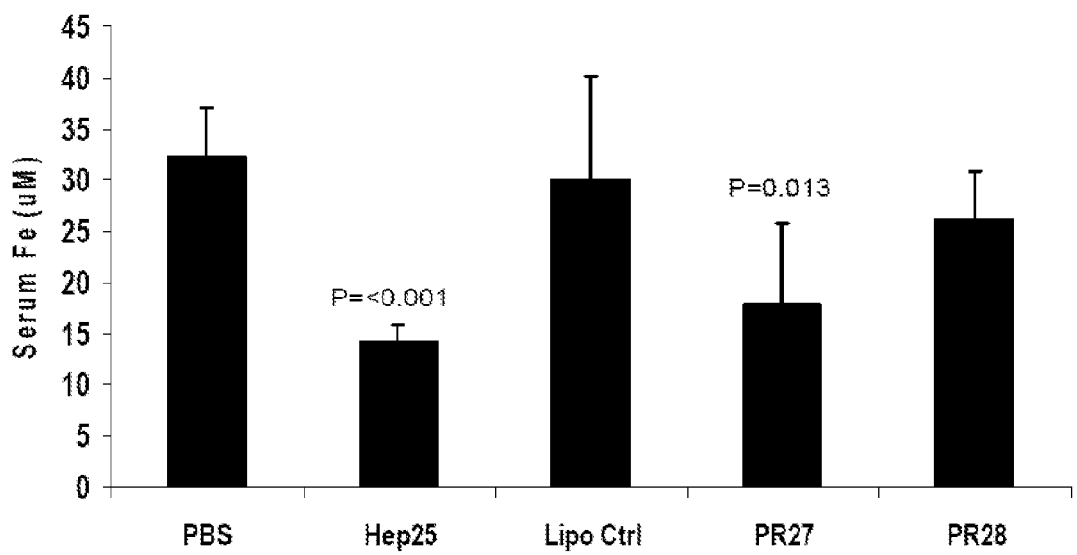
FIG. 8 is a graph showing in vivo effect (as measured by serum iron levels in mice) of mini-hepcidins Pr27 and Pr28 which were first mixed with liposomes and injected intraperitoneally (20 nmoles). The amount of injected Hep25 was 20 nmoles.

As shown in FIG. 8, i.p. administration of 20 nmoles Pr27 in liposomal solution also caused a serum iron decrease similar to that caused by i.p. administration of 20 nmoles Hep25. Administration of liposomal solution by itself did not affect serum iron levels. The liposomal solution was prepared by mixing 100 µl of PBS with 500 µg empty liposomes COATSOME EL series (NOF, Tokyo, Japan) (prepared as per manufacturer's recommendation). Mini-hepcidin Pr28 dissolved in liposomal solution, however, showed lesser ability to decrease serum iron than Pr27. The experiment indicates that suspension of peptides in liposomes does not affect their activity. Thus, liposomes may be useful for oral administration of peptides according to the present invention.

Figure 9:
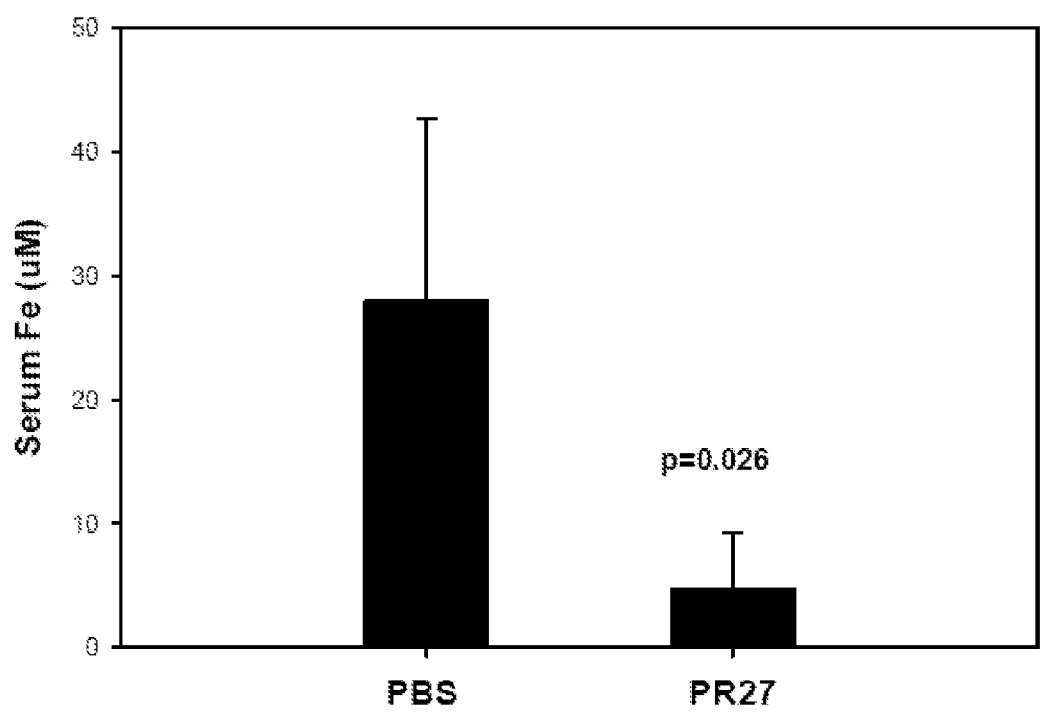
FIG. 9 is a graph showing in vivo effect (as measured by serum iron levels in mice) of mini-hepcidin Pr27 after oral administration by gavage (200 nmoles).

As shown in FIG. 9, oral administration of Pr27 200 nmoles by gavage in a cremophore EL solution caused a decrease in serum iron in mice as compared to oral administration of PBS in the same formulation. Cremophor EL increases solubility of chemicals, and is frequently used excipient or additive in drugs. Cremophor EL solution was prepared by mixing Cremophor EL (Sigma), ethanol and PBS in a ratio 12.5:12.5:75. 250 μl of the solution was administered by gavage to mice.

Thus, the present invention may be used to decrease serum iron in subjects. A preferred mini-hepcidin according to the present invention is a retroinverted peptide which comprises a PEG molecule, such as PEG11, linked to its N-terminal amino acid. In some embodiments, the PEG molecule is linked to palmitoyl group or diaminopropionic acid linked to one or more palmitoyl groups.

In addition to assaying the effect on serum iron content, other in vivo assays known in the art may be conducted to identify mini-hepcidins according to the present invention and/or determine the therapeutically effective amount of a given peptide or mini-hepcidin according to the present invention. Examples of such assays include the following:

Tissue iron assay. In addition to or instead of the serum iron assay above, tissue iron distribution can be determined by enhanced Perl's stain of liver and spleen sections obtained from the treated mice. Briefly, the tissue sections are fixed in 4% paraformaldehyde/PBS, incubated in Perl's solution (1:1, 2% HCl and 2% potassium ferrocyanide) and diaminobenzidine in 0.015% hydrogen peroxide. Tissue non-heme iron may be quantitated using the micromethod of Rebouche et al. See Rebouche et al., J Biochem Biophys Methods. 2004 Mar. 31; 58(3):239-51.; Pak et al. Blood. 2006 Dec. 1; 108(12): 3730-5. 100 mg pieces of liver and spleen are homogenized and acid is added to release non-heme bound iron which is detected by colorimetric reaction using ferrozine and compared to controls. Treatment with mini-hepcidins would be expected to cause redistribution of iron from other tissues to the spleen. Over weeks to months, the administration of mini-hepcidins would be expected to decrease tissue iron content in all tissues because of diminished dietary iron absorption.

Hematology assays. Hematology assays may be used to identify mini-hepcidins according to the present invention and/or determine the therapeutically effective amount of a given peptide or mini-hepcidin according to the present invention. Briefly, blood from treated subjects is collected into heparin-containing tubes. Hemoglobin, RBC, MCV, EPO, white cell parameters, reticulocyte counts, and reticulocyte Hgb content are determined using methods known in the art and compared to controls. Treatment with mini-hepcidins would be expected to cause a decrease in MCV and diminish the Hgb content of reticulocytes. Administration of mini-hepcidins in excessive amounts would be expected to decrease Hgb.

IRON EXPORT ASSAYS. Iron ($^{55}$Fe) export assays known in the art using primary hepatocytes and macrophages may be used to identify mini-hepcidins according to the present invention and/or determine the therapeutically effective amount of a given peptide or mini-hepcidin according to the present invention. Peptides having hepcidin activity will diminish or decrease the release of $^{55}$Fe from cells. Briefly, cells are incubated with $^{55}$Fe-NTA or $^{55}$Fe-Tf for 36 hours. After washing off unincorporated $^{55}$Fe, cells are treated with a given peptide or a control. In case of ferroportin mutants, the transfection is performed prior to addition of $^{55}$Fe and expression allowed to proceed during the 36 hour iron-loading period. Aliquots of the media are collected after 1, 4, 8, 24, 36, 48 and 72 hours and radioactivity is determined by a scintillation counter. Cell-associated radioactivity can be measured by centrifuging cells through silicone oil to lower the non-specific binding of radiolabeled iron to cells using methods known in the art.

To determine whether a given peptide modifies the internalization and degradation of endogenous ferroportin, the protein levels and cellular distribution of ferroportin in hepatocytes and macrophages treated with the peptide may be assayed using Western blotting, immunohistochemistry and ferroportin antibodies known in the art.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

We claim:

1. An isolated peptide consisting of the following structural formula

A1-A2-A3-A4-A5-A6-A7-A8-A9-A10 wherein
- A1 is Asp, Glu, pyroglutamate, Gln, Asn, D-Asp, D-Glu, D-pyroglutamate, D-Gln, D-Asn, bhAsp, Ida, or N-MeAsp, Ala, D-Ala, Cys, D-Cys, Phe, D-Phe, Asp or D-Asp, or Dpa or (D)Dpa;
- where if A1 is Asp or D-Asp, A2 is Cys or D-Cys, if A1 is Phe or D-Phe the n-terminus is optionally attached to a PEG molecule linked to chenodeoxvcholate, ursodeoxvcholate, or palmitoyl, or if A1 is Dpa or (D)Dpa is attached at the n-terminus to palmitoyl,
- A2 is Thr, Ser, Val, Ala, D-Thr, D-Ser, D-Val, Tle, Inp, Chg, bhThr, N-MeThr, D-Ala, Cys, D-Cys, Pro, D-Pro, Gly, or D-Gly;
- A3 is His, D-His, Dpa, (D)Dpa, or 2-aminoindane;
- A4 is Phe, D-Phe, bhPhe, Dpa, Bip, lNal, bhDpa, Amc, PheF5, hPhe, Igl, or cyclohexylalanine;
- A5 is Pro, D-Pro, Oic, bhPro, trans-4-PhPro, cis-4-PhPro, cis-5-PhPro, or Idc;
- A6 is Ile, D-Ile, Phg, Chg, Amc, bhIle, Ach, or MeIle;
- A7 is Cys, D-Cys, Cys(S-tBut), homoC, Pen, or (D)Pen;
- A8 is Ile, D-Ile, Chg, Dpa, bhIle, Ach, or MeIle;
- A9 is Phe, Leu, Ile, Tyr, D-Phe, D-Leu, D-Ile, PheF5, N-MePhe, benzylamide, bhPhe, Dpa, Bip, 1Nal, bhDpa, cyclohexylalanine, Asp, D-Asp, or cysteamide,
- wherein Phe or D-Phe are optionally linked at the n-terminus to RA, Asp or D-Asp are optionally linked at the n-terminus to RB, bhPhe is linked to RC,
- wherein RA is -CONH-CH2-CH2-S-, or D-Pro linked to Pro-Lys or Pro-Arg, or bhPro linked to Pro linked to Pro-Lys or Pro-Arg, or D-Pro linked to bhPro Lys or bhPro-Arg,
- wherein RB is -PEG 11-GYIPEAPRDGQAYVRKD-GEWVLLSTFL, or -(PEG 11)-(GPHyp)$_{10}$,
- wherein RC is -D-Pro linked to Pro-Lys or ProArg, or -D-Pro linked to bhPro-Lys or bhPro-Arg; and
- A10 is Cys, Ser, Ala, D-Cys, D-Ser, or D-Ala;
- wherein the carboxy-terminal amino acid is in amide or carboxy- form;
- wherein at least one sulfhydryl amino acid is present as one of the amino acids in the sequence;
- wherein A1, A2, A1 to A2, A10, A9 to A10, or a combination thereof are optionally absent wherein
- bhAsp is 3-aminopentanedioic acid,
- Ida is 2,2'-azanediyldiacetic acid,
- N-MeAsp is (methylamino)pentanedioic acid,
- Tle is L-tert-leucine,
- Inp is isonipecotic acid,
- Chg is L-α-cyclohexylglycine,
- N-MeThr is (2S)-3-hydroxy-2-(methylamino)butanoic acid,
- Dpa is 3,3-diphenyl-L-alanine,
- (D)Dpa is 3,3-diphenyl-D-alanine,
- bhPhe is (S)-2-amino-4-phenylbutanoic acid,
- Bip is L-biphenylalanine,
- 1Nal is (1-naphthyl)-L-alanine,
- bhDpa is (S)-3-Amino-4,4-diphenylbutanoic acid,
- Amc is 4-(aminomethyl)cyclohexane carboxylic acid,
- PheF5 is (S)-2-amino-3-(perfluorophenyl)propanoic acid,
- hPhe is (S)-2-amino-4-phenylbutanoic acid,
- Igl is (S)-2-amino-2-(2,3-dihydro-1H-inden-2-yl)acetic acid,
- Oic is octahydroindole-2-carboxylic acid,
- bhPro is L-β-homoproline,
- trans-4-PhPro is (2S,4S)-4-phenylpyrrolidine-2-carboxylic acid,
- cis-4-PhPro is (2S,4S)-4-phenylpyrrolidine-2-carboxylic acid,
- cis-5-PhPro is (2S,5R)-5-phenylpyrrolidine-2-carboxylic acid,
- Idc is (R)-2-methylindoline,
- Phg is L-phenylglycine,
- Amc is 4-(aminomethyl)cyclohexane carboxylic acid,
- bhIle is (3R)-3-amino-4-methylhexanoic acid,
- Ach is 1-aminocyclohexane-1-carboxylic acid,
- MeIle is (3R)-4-methyl-3-(methylamino)hexanoic acid,
- Cys(S-tBut) is S-t-Butylthio-L-cysteine,
- homoC is L-homocysteine,
- Pen is L-Penicillamine, and
- (D)Pen is D-Penicillamine GPHyp is Gly-Pro-HydroxyPro.

2. The peptide of claim 1, wherein A1 is Asp, A2 is Thr, A3 is His, A4 is Phe, A5 is Pro, A6 is Ile, A7 is Cys, D-Cys, Cys(S-tBut), homoC, Pen, or (D)Pen, A8 is Ile, A9 is Phe in amide form, and A10 is absent.

3. The peptide of claim 1, wherein A1 and A2 are absent, A3 is His, A4 is Phe, A5 is Pro, A6 is Ile, A7 is Cys D-Cys, Cys(S-tBut), homoC, Pen, or (D)Pen, A8 is Ile in amide form, and A9 and A10 are absent.

4. The peptide of claim 1, wherein A1 and A2 are absent, A3 is His, A4 is Phe, A5 is Pro, A6 is Ile, A7 is Cys D-Cys, Cys(S-tBut), homoC, Pen, or (D)Pen, and A8 to A10 are absent, where the C-terminus is in amide form.

5. The peptide of claim 1, wherein the peptide is a cyclic peptide.

6. The peptide of according to claim 1, wherein the sequence is retroinverted such that A1 is the C-terminus and A10 is the N-terminus.

7. An isolated peptide consisting of the following structural formula

A1-A2-A3-A4-A5-A6-A7-A8-A9-A10 wherein
- A1 is Asp, Glu, pyroglutamate, Gln, Asn, D-Asp, D-Glu, D-pyroglutamate, D-Gln, D-Asn, bhAsp, Ida, or N-MeAsp, Ala, D-Ala, Cys, D-Cys, Phe, D-Phe, Asp or D-Asp, or Dpa or (D)Dpa;
- where if A1 is Asp or D-Asp, A2 is Cys or D-Cys, if A1 is Phe or D-Phe the n-terminus is optionally attached to a PEG molecule linked to chenodeoxvcholate, ursodeoxvcholate, or palmitoyl, or if A1 is Dpa or (D)Dpa is attached at the n-terminus to palmitoyl, A2 is Thr, Ser, Val, Ala, D-Thr, D-Ser, D-Val, Tle, Inp, Chg, N-MeThr, D-Ala, Cys, D-Cys, Pro, D-Pro, Gly, or D-Gly;
A3 is His, D-His, Dpa, (D)Dpa, or 2-aminoindane;
A4 is Phe, D-Phe, bhPhe, Dpa, Bip, lNal, bhDpa, Amc, PheF5, hPhe, Igl, or cyclohexylalanine;
A5 is Pro, D-Pro, Oic, bhPro, trans-4-PhPro, cis-4-Ph-Pro, cis-5-PhPro, or Idc;
A6 is Ile, D-Ile, Phg, Chg, Amc, bhIle, Ach, or MeIle;
A7 is Cys, D-Cys, Cys(S-tBut), homoC, Pen, (D)Pen, or Dap(AcBr);
A8 is Ile, D-Ile, Chg, Dpa, bhIle, Ach, or MeIle;
A9 is Phe, Leu, Ile, Tyr, D-Phe, D-Leu, D-Ile, PheF5, N-MePhe, benzylamide, bhPhe, Dpa, Bip, 1Nal, bhDpa, cyclohexylalanine, Asp, D-Asp, or cysteamide,
wherein Phe or D-Phe are optionally linked at the n-terminus to RA, Asp or D-Asp are optionally linked at the n-terminus to RB, bhPhe is linked to RC,
wherein RA is -CONH-CH2-CH2-S-, or D-Pro linked to Pro-Lys or Pro-Arg, or bhPro linked to Pro linked to Pro-Lys or Pro-Arg, or D-Pro linked to bhPro Lys or bhPro-Arg,
wherein RB is -PEG 11-GYIPEAPRDGQAYVRKD-GEWVLLSTFL, or -(PEG 11)-(GPHyp)$_{10}$,
wherein RC is -D-Pro linked to Pro-Lys or ProArg, or -D-Pro linked to bhPro-Lys or bhPro-Arg; and
A10 is Cys, Ser, Ala, D-Cys, D-Ser, or D-Ala;
wherein the carboxy-terminal amino acid is in amide or carboxy- form;
wherein at least one sulfhydryl amino acid is present as one of the amino acids in the sequence; and
wherein A1, A2, A1 to A2, A10, A9 to A10, or a combination thereof are optionally absent,
wherein the peptide has -CONH$_2$-CH$_2$-CH$_2$-S, Chenodeoxycholate-(PEG11)-, Ursodeoxycholate-(PEG11)-, Palmitoyl-(PEG11)-, 2(Palmitoyl)-diaminopropionic acid-(PEG11)-, -PEG11-GYIPEAPRDGQAYVRKDGEWVLLSTFL, -(PEG11)-(Gly-Pro-hydroxyproline)10, -(D)P-PK, -(D)P-PR, -bh-ProPK, -bhProPR, (D)P-bhProK, or -(D)P-bhProR at the N-terminus, C-terminus, or both,
wherein
bhAsp is 3-aminopentanedioic acid,
Ida is 2,2'-azanediyldiacetic acid,
N-MeAsp is (methylamino)pentanedioic acid,
Tle is L-tert-leucine,
Inp is isonipecotic acid,
Chg is L-a-cyclohexylglycine,
N-MeThr is (2S)-3-hydroxy-2-(methylamino)butanoic acid,
Dpa is 3,3-diphenyl-L-alanine,
(D)Dpa is 3,3-diphenyl-D-alanine,
bhPhe is (S)-2-amino-4-phenylbutanoic acid,
Bip is L-biphenylalanine,
1Nal is (1-naphthyl)-L-alanine,
bhDpa is (S)-3-Amino-4,4-diphenylbutanoic acid,
Amc is 4-(aminomethyl)cyclohexane carboxylic acid,
PheF5 is (S)-2-amino-3-(perfluorophenyl)propanoic acid,
hPhe is (S)-2-amino-4-phenylbutanoic acid,
Igl is (S)-2-amino-2-(2,3-dihydro-1H-inden-2-yl)acetic acid,
Oic is octahydroindole-2-carboxylic acid,
bhPro is L-β-homoproline,
trans-4-PhPro is (2S,4S)-4-phenylpyrrolidine-2-carboxylic acid,
cis-4-PhPro is (2S,4S)-4-phenylpyrrolidine-2-carboxylic acid,
cis-5-PhPro is (2S,5R)-5-phenylpyrrolidine-2-carboxylic acid,
Idc is (R)-2-methylindoline,
Phg is L-phenylglycine,
Amc is 4-(aminomethyl)cyclohexane carboxylic acid,
bhIle is (3R)-3-amino-4-methylhexanoic acid,
Ach is 1-aminocyclohexane-1-carboxylic acid,
MeIle is (3R)-4-methyl-3-(methylamino)hexanoic acid,
Cys(S-tBut) is S-t-Butylthio-L-cysteine,
homoC is L-homocysteine,
Pen is L-Penicillamine, and
(D)Pen is D-Penicillamine GPHyp is Gly-Pro-HydroxyPro.

8. A peptide selected from the group consisting of
H-F-P-I-C-I,
H-F-P-I-C-I-F,
D-T-H-F-P-I-C-I-D-T-H-F-P-I-C-I-F,
D-T-H-F-P-I-A-I-F-C,
D-T-H-A-P-I-C-I-F,
D-T-H-A-P-I-CS-S-tBut-I-F,
D-T-H-F-P-I-C-I-F,
D-T-H-F-P-I-homoC-I-F,
D-T-H-F-P-I-Pen-I-F,
D-T-H-F-P-I-(D)Pen-I-F,
C-D-T-H-F-P-I-C-I-F,
D-Tle-H-Phg-Oic-Chg-C-Chg-F,
D-Tle-H-P-Oic-Chg-C-Chg-F,
(D)F-(D)I-(D)C-(D)I-(D)P-(D)F-(D)H-(D)T-(D)D,
(D)F-(D)I-(D)C-(D)I-(D)P-(D)F-(D)H,
R2-(D)F-(D)I-(D)C-(D)I-(D)P-(D)F-(D)H-(D)T-(D)D,
R3-(D)F-(D)I-(D)C-(D)I-(D)P-(D)F-(D)H-(D)T-(D)D,
(D)F-(D)I-(D)C-(D)I-(D)P-(D)F-(D)H-(D)T-(D)D-R6,
R4-(D)F-(D)I-(D)C-(D)I-(D)P-(D)F-(D)H-(D)T-(D)D,
R5-(D)F-(D)I-(D)C-(D)I-(D)P-(D)F-(D)H-(D)T-(D)D,
D-T-H-bhPhe-P-I-C-I-F,
D-T-H-Dpa-P-I-C-I-F,
D-T-H-Bip-P-I-C-I-F,
D-T-H-1Nal-P-I-C-I-F,
D-T-H-bhDpa-P-I-C-I-F,
D-T-H-F-P-I-C-I-bhPhe,
D-T-H-F-P-I-C-I-Dpa,
D-T-H-F-P-I-C-I-Bip,
D-T-H-F-P-I-C-I-1Nal,
D-T-H-F-P-I-C-I-bhDpa,
D-T-H-Dpa-P-I-C-I-Dpa,
D-Dpa-P-I-C-I-F,
D-Dpa-P-I-C-I-Dpa,
D-T-H-Dpa-P-R-C-R-Dpa,
D-T-H-Dpa-P-(D)R-C-(D)R-Dpa,
D-T-H-Dpa-Oic-I-C-I-F,
D-T-H-Dpa-Oic-I-C-I-Dpa,
D-T-H-Dpa-P-C-C-C-Dpa,
D-T-H-F-P-I-C-I-F-R8,
D-T-H-F-P-I-C-I-F-R9,
D-T-H-F-P-I-C-I-F-R10,
D-T-H-F-P-I-C-I-F-R11,
D-T-H-F-P-I-C-I-F-R12,
D-T-H-F-P-I-C-I-F-R13,
D-T-H-F-P-I-C-I-bhPhe-R8,
D-T-H-F-P-I-C-I-bhPhe-R9,
D-T-H-F-P-I-C-I-bhPhe-R12,
D-T-H-F-P-I-C-I-bhPhe-R13,
C-Inp-(D)Dpa-Amc-R-Amc-Inp-Dpa-Cysteamide,
C-P-(D)Dpa-Amc-R-Amc-Inp-Dpa-Cysteamide,
C-(D)P-(D)Dpa-Amc-R -Amc-Inp-Dpa-Cysteamide, and
C-G-(D)Dpa-Amc-R-Amc-Inp-Dpa-Cysteamide,
wherein R1 =-CONH$_2$-CH$_2$-CH$_2$-S, R2 =Chenodeoxycholate-(PEG11)-, R3 =Ursodeoxycholate-(PEG11)-, R4=Palmitoyl-(PEG11)-, R5=2(Palmitoyl)- diaminopropionic acid-(PEG11)- , R6=-PEG11 -GYIPEAPRDGQAYVRKDGEWVLLSTFL, R7=-(PEG11)- (Gly-Pro-hydroxyproline)10,R8=-(D)P-PK, R9=-(D)P-PR, R10=-bhProPK, R11=-bhProPR, R12=-(D)P-bhProK, and R13=-(D)P-bhProR, wherein
bhAsp is 3-aminopentanedioic acid,
Ida is 2,2'-azanediyldiacetic acid,
N-MeAsp is (methylamino)pentanedioic acid,
Tle is L-tert-leucine,
Inp is isonipecotic acid,
Chg is L-α-cyclohexylglycine,
N-MeThr is (2S)-3-hydroxy-2-(methylamino)butanoic acid,
Dpa is 3,3-diphenyl-L-alanine,
(D)Dpa is 3,3-diphenyl-D-alanine,
bhPhe is (S)-2-amino-4-phenylbutanoic acid,
Bip is L-biphenylalanine,
1Nal is (1-naphthyl)-L-alanine,
bhDpa is (S)-3-Amino-4,4-diphenylbutanoic acid,
Amc is 4-(aminomethyl)cyclohexane carboxylic acid,
PheF5 is (S)-2-amino-3-(perfluorophenyl)propanoic acid,
hPhe is (S)-2-amino-4-phenylbutanoic acid,
Igl is (S)-2-amino-2-(2,3-dihydro-1H-inden-2-yl)acetic acid,
Oic is octahydroindole-2-carboxylic acid,
bhPro is L-β-homoproline,
trans-4-PhPro is (2S,4S)-4-phenylpyrrolidine-2-carboxylic acid,
cis-4-PhPro is (2S,4S)-4-phenylpyrrolidine-2-carboxylic acid,
cis-5-PhPro is (2S,5R)-5-phenylpyrrolidine-2-carboxylic acid,
Idc is (R)-2-methylindoline,
Phg is L-phenylglycine,
Amc is 4-(aminomethyl)cyclohexane carboxylic acid,
bhIle is (3R)-3-amino-4-methylhexanoic acid,
Ach is 1-aminocyclohexane-1-carboxylic acid,
MeIle is (3R)-4-methyl-3-(methylamino)hexanoic acid,
Cys(S-tBut) is S-t-Butylthio-L-cysteine,
homoC is L-homocysteine,
Pen is L-Penicillamine, and
(D)Pen is D-Penicillamine.

9. The peptide according to claim 1, wherein the peptide exhibits hepcidin activity.

10. The peptide according to claim 1, wherein the peptide binds ferroportin.

11. A composition which comprises at least one peptide according to claim 1.

12. A method of binding a ferroportin or inducing ferroportin internalization and degradation which comprises contacting the ferroportin with at least one peptide according to claim 1.

13. A method of treating a disease of iron metabolism in a subject which comprises administering at least one peptide according to claim 1 to the subject.

14. The method of claim 13, wherein the disease of iron metabolism is an iron overload disease.

15. A kit comprising at least one peptide according to claim 1 packaged together with a reagent, a device, instructional material, or a combination thereof.

16. A complex comprising at least one peptide according to claim 1 bound to a ferroportin or an antibody.

17. An isolated peptide consisting of the following structural formula

A1-A2-A3-A4-A5-A6-A7-A8-A9-A10 wherein
A1 is Asp, Glu, pyroglutamate, Gln, Asn, D-Asp, D-Glu, D-pyroglutamate, D-Gln, D-Asn, bhAsp, Ida, or N-MeAsp, Ala, D-Ala, Cys, D-Cys, Phe, D-Phe, Asp or D-Asp, or Dpa or (D)Dpa;
where if A1 is Asp or D-Asp, A2 is Cys or D-Cys, if A1 is Phe or D-Phe the n-terminus is optionally attached to a PEG molecule linked to chenodeoxycholate, ursodeoxycholate, or palmitoyl, or if A1 is Dpa or (D)Dpa is attached at the n-terminus to palmitoyl,
A2 is Thr, Ser, Val, Ala, D-Thr, D-Ser, D-Val, Tle, Inp, Chg, N-MeThr, D-Ala, Cys, D-Cys, Pro, D-Pro, Gly, or D-Gly;
A3 is His;
A4 is Phe;
A5 is Pro;
A6 is Ile;
A7 is Cys, D-Cys, Cys(S-tBut), or homoC;
A8 is Ile;
A9 is Phe, Leu, Ile, Tyr, D-Phe, D-Leu, D-He, PheF5, N-MePhe, benzylamide, bhPhe, Dpa, Bip, 1Nal, bhDpa, cyclohexylalanine, Asp, D-Asp, or cysteamide,
wherein Phe or D-Phe are optionally linked at the n-terminus to RA, Asp or D-Asp are optionally linked at the n-terminus to RB, bhPhe is linked to RC,
wherein RA is -CONH-CH2-CH2-S-, or D-Pro linked to Pro-Lys or Pro-Arg, or bhPro linked to Pro linked to Pro-Lys or Pro-Arg, or D-Pro linked to bhPro Lys or bhPro-Arg,
wherein RB is -PEG 11-GYIPEAPRDGQAYVRKDGEWVLLSTFL, or -(PEG 11)-(GPHyp)$_{10}$,
wherein RC is -D-Pro linked to Pro-Lys or ProArg, or -D-Pro linked to bhPro-Lys or bhPro-Arg; and
A10 is Cys, Ser, Ala, D-Cys, D-Ser, or D-Ala;
wherein the carboxy-terminal amino acid is in amide or carboxy- form;
wherein at least one sulfhydryl amino acid is present as one of the amino acids in the sequence; and
wherein A1, A2, A1 to A2, A10, A9 to A10, or a combination thereof are optionally absent
wherein
bhAsp is 3-aminopentanedioic acid,
Ida is 2,2'-azanediyldiacetic acid,
N-MeAsp is (methylamino)pentanedioic acid,
Tle is L-tert-leucine,
Inp is isonipecotic acid,
Chg is L-α-cyclohexylglycine,
N-MeThr is (2S)-3-hydroxy-2-(methylamino)butanoic acid,
Dpa is 3,3-diphenyl-L-alanine,
(D)Dpa is 3,3-diphenyl-D-alanine,
bhPhe is (S)-2-amino-4-phenylbutanoic acid,
Bip is L-biphenylalanine,
1Nal is (1-naphthyl)-L-alanine,
bhDpa is (S)-3-Amino-4,4-diphenylbutanoic acid,
Amc is 4-(aminomethyl)cyclohexane carboxylic acid,
PheF5 is (S)-2-amino-3-(perfluorophenyl)propanoic acid,
hPhe is (S)-2-amino-4-phenylbutanoic acid,
Igl is (S)-2-amino-2-(2,3-dihydro-1H-inden-2-yl)acetic acid,
Oic is octahydroindole-2-carboxylic acid,
bhPro is L-β-homoproline,
trans-4-PhPro is (2S,4S)-4-phenylpyrrolidine-2-carboxylic acid, cis-4-PhPro is (2S,4S)-4-phenylpyrrolidine-2-carboxylic acid,
cis-5-PhPro is (2S,5R)-5-phenylpyrrolidine-2-carboxylic acid,
Idc is (R)-2-methylindoline,
Phg is L-phenylglycine,
Amc is 4-(aminomethyl)cyclohexane carboxylic acid,
bhIle is (3R)-3-amino-4-methylhexanoic acid,
Ach is 1-aminocyclohexane-l-carboxylic acid,
MeIle is (3R)-4-methyl-3-(methylamino)hexanoic acid,
Cys(S-tBut) is S-t-Butylthio-L-cysteine,
homoC is L-homocysteine,
Pen is L-Penicillamine, and
(D)Pen is D-Penicillamine.

18. The isolated peptide of claim 1, wherein the peptide binds to ferroportin with an $EC_{50}$ of about 1000 nM or less.

* * * * *

UNITED STATES PATENT AND TRADEMARK OFFICE
CERTIFICATE OF CORRECTION

PATENT NO. : 8,435,941 B2
APPLICATION NO. : 13/131792
DATED : May 7, 2013
INVENTOR(S) : Ganz et al.

It is certified that error appears in the above-identified patent and that said Letters Patent is hereby corrected as shown below:

In the Claims:

In Column 31, line 34:
 Please change "D-He," to -- D-Ile, --;

In Column 31, line 41:
 Please change "-CONH-CH2-CH2-S-" to -- -CONH-$CH_2$-$CH_2$-S- --;

In Column 31, line 43:
 Please change "bhPro Lys" to -- bhPro-Lys --;

In Column 32, line 34:
 Please change "Pen is L-Penicillamine, and" to -- Pen is L-Penicillamine, --;

In Column 32, line 35:
 Please change "(D)Pen is D-Penicillamine GPHyp is Gly-Pro-Hydrox-" to
-- (D)Pen is D-Penicillamine, and --;

In Column 32, line 36:
 Please change "yPro." to -- GPHyp is Gly-Pro-HydroxyPro. --;

In Column 32, line 44:
 Please change "A9and A10" to -- A9 and A10 --;

In Column 33, line 13:
 Please change "D-He," to -- D-Ile, --;

In Column 33, line 20:
 Please change "-CONH-CH2-CH2-S-" to -- -CONH-$CH_2$-$CH_2$-S- --;

Signed and Sealed this
Twenty-fourth Day of September, 2013

Teresa Stanek Rea
*Deputy Director of the United States Patent and Trademark Office*

CERTIFICATE OF CORRECTION (continued)
U.S. Pat. No. 8,435,941 B2

In Column 33, line 22:
    Please change "bhPro Lys" to -- bhPro-Lys --;

In Column 34, line 13:
    Please change "Pen is L-Penicillamine, and" to -- Pen is L-Penicillamine, --;

In Column 34, line 14:
    Please change "(D)Pen is D-Penicillamine GPHyp is Gly-Pro-Hydrox-" to
-- (D)Pen is D-Penicillamine, and --;

In Column 34, line 15:
    Please change "yPro." to -- GPHyp is Gly-Pro-HydroxyPro. --;

In Column 36, line 21:
    Please change "D-He," to -- D-Ile, --;

In Column 36, line 28:
    Please change "-CONH-CH2-CH2-S-" to -- -CONH-$CH_2$-$CH_2$-S- --.